(12) United States Patent
Hagner et al.

(10) Patent No.: US 8,317,022 B2
(45) Date of Patent: *Nov. 27, 2012

(54) PACKAGE OF FOLDED DISPOSABLE ABSORBENT PANTS

(75) Inventors: Todd Ralph Hagner, Neenah, WI (US); Gregory James Fries, Hubertus, WI (US); George Ikuya Nukuto, Wexford, PA (US); Jennifer Lea Westemeyer, Appleton, WI (US); Cynthia Lee Hogan, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/858,969

(22) Filed: Aug. 18, 2010

(65) Prior Publication Data

US 2012/0043244 A1 Feb. 23, 2012

(51) Int. Cl.
*B65D 85/16* (2006.01)
*B65D 73/00* (2006.01)
*A61F 13/15* (2006.01)

(52) U.S. Cl. .................... 206/494; 206/776; 604/385.01

(58) Field of Classification Search .................. 206/494, 206/440, 781, 782, 776, 769, 581, 459.5, 206/812, 499; 604/385.27, 385.01, 385.24
See application file for complete search history.

(56) References Cited

U.S. PATENT DOCUMENTS

| | | | |
|---|---|---|---|
| 3,332,545 A | 7/1967 | Vranesic | |
| 3,878,941 A | 4/1975 | Kelner | |
| 4,648,505 A * | 3/1987 | Belmondo | 206/214 |
| 4,802,884 A * | 2/1989 | Froidh et al. | 493/339 |
| 4,940,464 A | 7/1990 | Van Gompel et al. | |
| D312,208 S | 11/1990 | Sorkin | |
| 5,934,470 A | 8/1999 | Bauer et al. | |
| 5,967,665 A | 10/1999 | MacDonald et al. | |
| 6,024,219 A | 2/2000 | Froehlich et al. | |
| 6,079,562 A * | 6/2000 | Bauer et al. | 206/494 |
| 6,318,555 B1 * | 11/2001 | Kuske et al. | 206/494 |

(Continued)

FOREIGN PATENT DOCUMENTS

EP 0988846 A2 3/2000

(Continued)

OTHER PUBLICATIONS

Description of Depend® Protective Underwear, commercially available in 1998 in the United States.

(Continued)

*Primary Examiner* — Steven A. Reynolds
(74) *Attorney, Agent, or Firm* — R. Joseph Foster, III; H. Michael Kubicki

(57) ABSTRACT

The package includes a housing portion having a transparent window region. A plurality of disposable absorbent pants is disposed within the housing portion. Each pant defines a waistband region which abuts a waist end. Each waistband region comprises a front waistband portion and a back waistband portion. Each pant further defines a crotch region which abuts a crotch end. At least a first pant is folded and positioned such that at least a portion of the waistband region of the first pant is visible through the transparent window region. Specified portions of the first pant may be obscured by an opaque border region. The first pant may include a back-label indicator that is visible through the transparent window region. A second pant may also be visible through the transparent window region.

25 Claims, 16 Drawing Sheets

U.S. PATENT DOCUMENTS

| | | |
|---|---|---|
| 6,491,165 B2 | 12/2002 | Kuske et al. |
| 6,601,705 B2 | 8/2003 | Molina et al. |
| 6,702,798 B2 * | 3/2004 | Christoffel et al. .... 604/385.201 |
| 7,021,466 B2 | 4/2006 | Kuske et al. |
| 7,237,370 B1 | 7/2007 | Garone et al. |
| 7,694,818 B2 * | 4/2010 | Molina et al. ................. 206/494 |
| 2002/0162766 A1 | 11/2002 | Saso et al. |
| 2003/0070955 A1 | 4/2003 | Kuske et al. |
| 2004/0102748 A1 | 5/2004 | Hirotsu |
| 2004/0173490 A1 * | 9/2004 | Otsubo ......................... 206/440 |
| 2004/0211696 A1 * | 10/2004 | Underhill et al. ............. 206/494 |
| 2005/0133395 A1 * | 6/2005 | Mishima et al. ............. 206/438 |
| 2006/0131200 A1 * | 6/2006 | Boldra et al. ................. 206/494 |
| 2006/0231448 A1 | 10/2006 | Clough |
| 2007/0043331 A1 | 2/2007 | Haruki et al. |
| 2007/0144937 A1 | 6/2007 | Gilroy |
| 2007/0267322 A1 * | 11/2007 | Kishida et al. ................ 206/776 |
| 2008/0110984 A1 | 5/2008 | Uchitani |
| 2008/0264828 A1 | 10/2008 | Benson et al. |
| 2010/0072108 A1 | 3/2010 | Underhill et al. |
| 2011/0192749 A1 | 8/2011 | Hooyman et al. |

FOREIGN PATENT DOCUMENTS

| | | |
|---|---|---|
| JP | 64-009177 | 1/1989 |
| JP | 2000-024029 A | 1/2000 |
| JP | 2001-019070 A | 1/2001 |
| WO | WO 02/07665 A1 | 1/2002 |
| WO | WO 2004/108043 A1 | 12/2004 |

OTHER PUBLICATIONS

Description and photographs of Kotex® Personals® Disposable Protective Panties, commercially available in 1998 in the United States.

* cited by examiner

PACKAGE OF FOLDED DISPOSABLE ABSORBENT PANTS

BACKGROUND

People rely on disposable absorbent garments in their everyday lives, including such garments as adult incontinence products, enuresis pants, training pants, and diapers. Many manufacturers seek to better meet the needs of users of such products. With certain products, such as adult incontinence underwear and enuresis pants, it is important that the garments look and feel as much as possible like "regular" underwear to promote an improved sense of normalcy to the wearer who suffers from incontinence or enuresis. Additionally, purchasers and users of such products are frequently embarrassed about their condition and about having to purchase products to deal with their incontinence or enuresis condition.

Currently, the most common method for obtaining incontinence and enuresis underwear is by purchasing relatively large bags in retail stores. Such conventional packages of incontinence and enuresis underwear are opaque or mostly opaque, which some purchasers may perceive as overly "diaper-like" or too strongly connoting the presence of a personal care absorbent product directed to a urinary condition. Such conventional packaging bears little resemblance to the packaging in which durable clothing is sold. There is a need for a package of incontinence or enuresis underwear that better resembles a package of durable underwear so as to improve the feeling of normalcy for the purchaser/user. There is also a need for a package of incontinence or enuresis underwear that allows the potential purchaser to see selected features of the underwear, such as, for example, cloth-like material used to make the underwear, elastic waistbands, and back-label indicators.

Attempts have been made in the art to provided windowed packages to allow consumers to inspect the absorbent garments contained within the sealed packages prior to purchase. See, for example, U.S. Pat. No. 6,318,555 to Kuske et al. However, the prior art does not optimally provide for targeted display and/or obscurement of particular features of pants, particularly with larger underwear such as incontinence and enuresis underwear, some of which frequently require multiple folds in both directions to efficiently configure the underwear for commercial packaging and sale.

SUMMARY OF THE INVENTION

To better meet the above-described unmet needs in the art, a new package of disposable absorbent pants has been invented. In one embodiment, the package comprises a housing portion which defines a height dimension, a width dimension, and a depth dimension. The housing portion comprises a front wall and a back wall, each of which extends along the width and height dimensions, the front wall being spaced from the back wall in the depth dimension. The front wall comprises a transparent window region and an opaque border region. The package in this embodiment further includes a plurality of disposable absorbent pants disposed within the housing portion. Each pant defines a waist opening, two leg openings, a waist end, and a crotch end, and each pant defines both a longitudinal direction that extends from the waist end to the crotch end and a transverse direction that is perpendicular to the longitudinal direction. Each pant further defines first and second side portions and a center portion positioned transversely between the first side portion and the second side portion. Each pant further defines a waistband region which abuts the waist end and which extends in the transverse direction to at least partially encircle the waist opening. Each waistband region comprises a front waistband portion and a back waistband portion. Each pant further defines a crotch region which abuts the crotch end. Each of the plurality of pants is folded at least once in the longitudinal direction so as to position the crotch end in close proximity to the waist end, and each of the plurality of pants is folded twice in the transverse direction such that the first and second side portions of each pant are folded over the respective center portion. At least a first pant of the plurality of disposable absorbent pants is positioned within the housing portion such that the longitudinal direction of the first pant extends in the height dimension, and such that at least a portion of the waistband region of the first pant is visible through the transparent window region and such that the crotch end of the first pant is obscured by the opaque border region.

In another embodiment, the package comprises a housing portion which defines a height dimension, a width dimension, and a depth dimension. The housing portion comprises a front wall and a back wall, each of which extends along the width and height dimensions, the front wall being spaced from the back wall in the depth dimension. The front wall comprises a transparent window region and an opaque border region. The package in this embodiment further includes a plurality of disposable absorbent pants disposed within the housing portion. Each pant defines a waist opening, two leg openings, a waist end, and a crotch end, and each pant defines both a longitudinal direction that extends from the waist end to the crotch end and a transverse direction that is perpendicular to the longitudinal direction. Each pant further defines first and second side portions and a center portion positioned transversely between the first side portion and the second side portion. Each pant further defines a waistband region which abuts the waist end and which extends in the transverse direction to at least partially encircle the waist opening. Each waistband region comprises a front waistband portion and a back waistband portion. Each pant further defines a crotch region which abuts the crotch end. Each pant comprises an absorbent core having a front edge, a back edge spaced from the front edge in the longitudinal direction, and two side edges which extend from the front edge to the back edge. Each of the plurality of pants is folded at least once in the longitudinal direction so as to position the crotch end in close proximity to the waist end, and each of the plurality of pants is folded twice in the transverse direction such that the first and second side portions of each pant are folded over the respective center portion. At least a first pant of the plurality of disposable absorbent pants is positioned within the housing portion such that the longitudinal direction of the first pant extends in the height dimension, and such that at least a portion of the waistband region of the first pant is visible through the transparent window region and such that the front edge of the absorbent core of the first pant is obscured by the opaque border region.

In yet another embodiment, the package comprises a housing portion which defines a height dimension, a width dimension, and a depth dimension. The housing portion comprises a front wall and a back wall, each of which extends along the width and height dimensions, the front wall being spaced from the back wall in the depth dimension. The front wall comprises a transparent window region. The package in this embodiment further includes a plurality of disposable absorbent pants disposed within the housing portion. Each pant defines a waist opening, two leg openings, a waist end, and a crotch end, and each pant defines both a longitudinal direction that extends from the waist end to the crotch end and a transverse direction that is perpendicular to the longitudinal direction. Each pant further defines first and second side portions and a center portion positioned transversely between the first side portion and the second side portion. Each pant further defines a waistband region which abuts the waist end and which extends in the transverse direction to at least partially encircle the waist opening. Each waistband region comprises a front waistband portion and a back waistband portion. Each pant further defines a crotch region which abuts the crotch end. Each of the plurality of pants is folded at least once in the longitudinal direction so as to position the crotch end in close proximity to the waist end, and each of the plurality of pants is folded twice in the transverse direction such that the first and second side portions of each pant are folded over the respective center portion. At least a first pant of the plurality of disposable absorbent pants is positioned within the housing portion such that the longitudinal direction of the first pant extends in the height dimension, and such that at least a portion of the waistband region of the first pant is visible through the transparent window region. At least a second pant of the plurality of disposable absorbent pants is positioned within the housing portion such that the longitudinal direction of the second pant extends in the height dimension, and such that at least a portion of the waistband region of the second pant is visible through the transparent window region, the second pant being positioned alongside the first pant in the width dimension.

In still another embodiment, the package comprises a housing portion which defines a height dimension, a width dimension, and a depth dimension. The housing portion comprises a front wall and a back wall, each of which extends along the width and height dimensions, the front wall being spaced from the back wall in the depth dimension. The front wall comprises a transparent window region. The package in this embodiment further includes a plurality of disposable absorbent pants disposed within the housing portion. Each pant defines a waist opening, two leg openings, a waist end, and a crotch end, and each pant defines both a longitudinal direction that extends from the waist end to the crotch end and a transverse direction that is perpendicular to the longitudinal direction. Each pant further defines first and second side portions and a center portion positioned transversely between the first side portion and the second side portion. Each pant further defines a waistband region which abuts the waist end and which extends in the transverse direction to at least partially encircle the waist opening. Each waistband region comprises a front waistband portion and a back waistband portion. Each pant further defines a crotch region which abuts the crotch end. Each of the plurality of pants is folded at least once in the longitudinal direction so as to position the crotch end in close proximity to the waist end, and each of the plurality of pants is folded twice in the transverse direction such that the first and second side portions of each pant are folded over the respective center portion. At least a first pant of the plurality of disposable absorbent pants is positioned within the housing portion such that the longitudinal direction of the first pant extends in the height dimension, and such that at least a portion of the waistband region of the first pant is visible through the transparent window region. In this embodiment, the first pant includes a back-label indicator disposed on a bodyside surface of the first pant in close proximity to the back waistband portion of the first pant. The back-label indicator of the first pant is visible through the transparent window region.

By providing a housing portion and pants folded and positioned within the housing portion in the summary examples set forth above and in the examples that follow, selected features of the pants can be highlighted for inspection, or hidden from inspection, to engage a purchaser/consumer and to optimize the visual presentation of the package of pants.

DEFINITIONS

Figure 1:
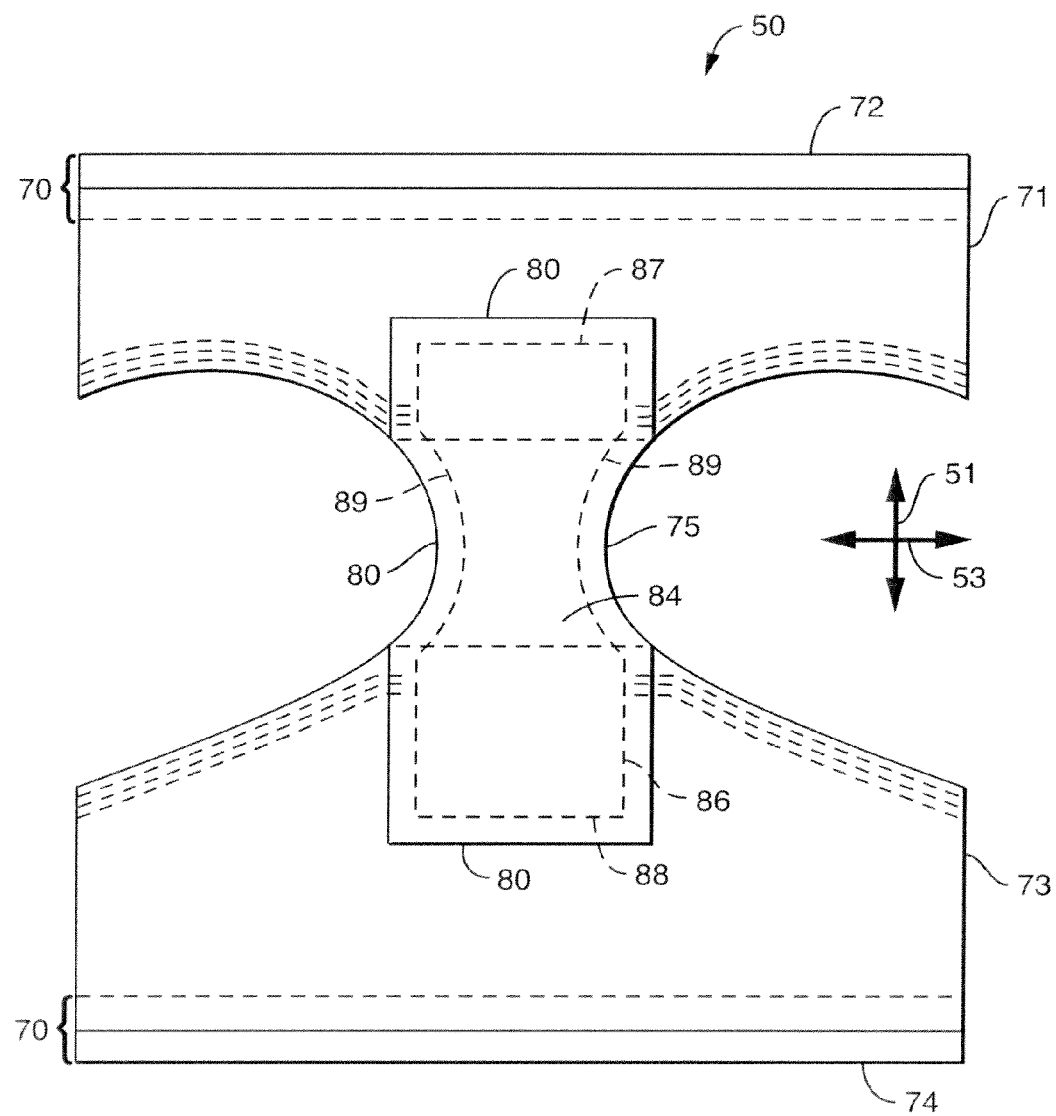
FIG. 1 representatively illustrates a plan view of one embodiment of a disposable absorbent pant suitable for use in conjunction with certain embodiments of the present invention in a longitudinally stretched and laid-flat condition, prior to the joining of the front and back waist regions, and showing the surface of the article that faces the wearer when the article is worn.
Figure 2:
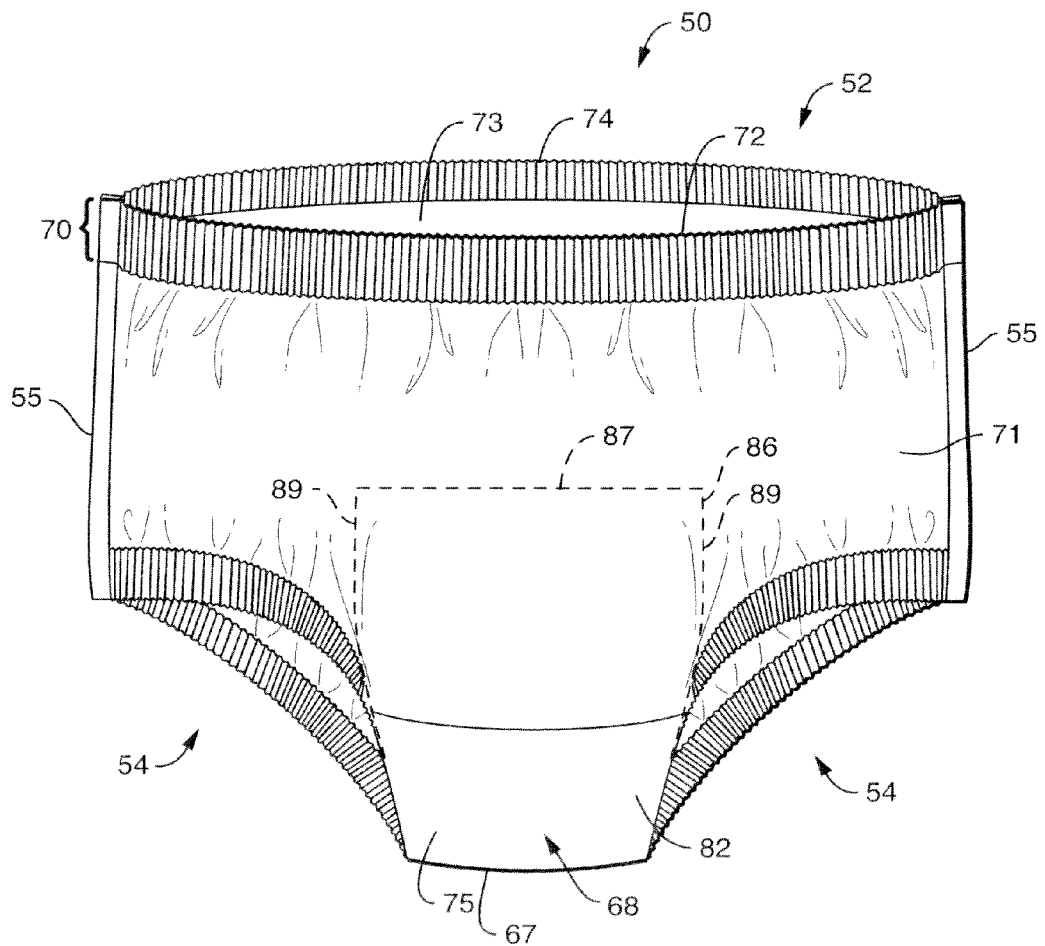
FIG. 2 representatively illustrates a front perspective view of the exemplary embodiment of FIG. 1, shown in a fully assembled condition.

Within the context of this specification, each term or phrase below will include the following meaning or meanings. Additional terms are defined elsewhere in the specification.

"Attached" refers to the joining, adhering, bonding, connecting, or the like, of two elements. Two elements will be considered to be attached together when they are attached directly to one another or indirectly to one another, such as when each is directly attached to intermediate elements.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 20 percent of its elongation. It is generally preferred that the elastomeric material or composite be capable of being elongated by at least 100 percent, more preferably by at least 200 percent, of its relaxed length and recover, upon release of an applied force, at least 50 percent of its elongation.

"Integral" is used to refer to various portions of a single unitary element rather than separate structures bonded to or placed with or placed near one another.

"Layer" when used in the singular can have the dual meaning of a single element or a plurality of elements.

"Longitudinal" and "transverse" have their customary meaning, as indicated by the longitudinal and transverse axes depicted in the Figures. The longitudinal axis lies in the plane of the article and is generally parallel to a vertical plane that bisects a standing wearer into left and right body halves when the article is worn. The transverse axis lies in the plane of the article generally perpendicular to the longitudinal axis.

These terms may be defined with additional language in the remaining portions of the specification.

DETAILED DESCRIPTION OF EXEMPLARY EMBODIMENTS

Reference to the Figures shall be made in describing various aspects and embodiments of the invention. It should be noted that the embodiments depicted in the Figures and described herein are merely representative examples of the pants and package of the invention. The various aspects and embodiments of the present invention are suitable for use with adult incontinence pants, prefastened disposable diapers, disposable swim pants, disposable training pants, disposable enuresis garments, and the like.

Referring to FIGS. 6-9 and 11, the invention relates to a package 10 of folded disposable absorbent pants 50. The package includes a housing portion 12. The housing portion 12 houses or contains the pants 50 by partially or completely forming an enclosure around the pants 50. The housing portion 12 defines a height dimension 16, a width dimension 17, and a depth dimension 18. The housing portion 12 includes a front wall 20 and a back wall 21, each of which extends along the height dimension 16 and the width dimension 17. The front wall 20 is spaced from the back wall 21 in the depth dimension 18. In particular embodiments, the housing portion 12 also includes a first side wall 23 and a second side wall 24, each of which extends along the height dimension 16 and the depth dimension 18. The first side wall 23 is spaced from the second side wall 24 in the width dimension 17. In particular embodiments, the housing portion 12 also includes a top wall 25 and a bottom wall 26, each of which extends along the width dimension 17 and the depth dimension 18. The top wall 25 is spaced from the bottom wall 26 in the height dimension 16.

The housing portion 12 of the package 10 may be formed of any suitable packaging material, such as, for example, plastic film, paperboard, corrugated board, flexible polymeric material, semi-rigid plastic, or combinations thereof. In one embodiment, the housing portion may comprise a plastic bag, such as a clear plastic bag. In another embodiment, the housing portion at least in part comprises a carton 27, such as a paperboard carton. The housing portion may optionally include one or more inserts disposed within the housing portion 12, such as a paperboard insert 14.

The front wall 20 includes an at least partially transparent window region 30 and an opaque border region 35. As described further below, the transparent window region is desirably configured to allow a consumer to view one or more portions of one or more pants disposed within the package 10, while the opaque border region is configured to obscure or block from view one or more portions of one or more pants disposed within the package 10.

The transparent window region 30 may be provided by any mechanism which allows a consumer to see through the front wall 20 into the interior of the housing portion 12. For example, in an embodiment in which the housing portion 12 comprises a carton, the transparent window region 30 can comprise an opening 31 in the carton 27. The opening 31 can be covered or sealed with a flexible or stiff translucent or transparent plastic material, or can be left uncovered and unsealed. If the entire carton 27 is constructed of a plastic material, such as a semi-rigid plastic material, the window region 30 can comprise a transparent or translucent portion of the carton 27. In another example, where the housing portion 12 comprises a bag 28, such as a plastic bag, the transparent window region 30 is defined by a transparent portion of the bag, as is representatively illustrated in FIGS. 8 and 9.

The opaque border region 35 may be provided by any mechanism which obscures or blocks from view one or more portions of one or more pants disposed within the package. In embodiments in which the housing portion comprises a carton 27, such as a paperboard carton, the opaque border region 35 can be defined by a portion of the carton 27. For example, in the embodiment depicted in FIGS. 6, 7, and 11, in which the housing portion 12 comprises a paperboard carton 27, the opaque border region 35 comprises paperboard. If the entire carton 27 is constructed of a plastic material, such as a semi-rigid plastic material or a flexible plastic bag 28, the opaque border region 35 can comprise an opaque insert, such as a paperboard insert 14, which is positioned within the housing portion 12, as is representatively illustrated in FIGS. 8 and 9. In another version where the entire housing portion 12 is constructed of a plastic material, such as a semi-rigid plastic material or a flexible plastic bag, the opaque border region 35 can comprise an opaque material, such as printed ink, coated onto the carton or bag.

The shape and size of the transparent window region 30 and of the opaque border region 35 may vary. For example, the opaque border region 35 may partially or fully border the transparent window region 30 on one or more sides of the transparent window region 30. In the example representatively illustrated in FIGS. 6, 7, and 11, the opaque border region 35 fully borders the transparent window region 30 on all four sides (that is, completely surrounds the transparent window region 30). In the example representatively illustrated in FIG. 8, the opaque border region 35 borders the transparent window region 30 only on the lower edge of the transparent window region 30—that is, the side of the window region that is closest to the bottom wall 26. In the example representatively illustrated in FIG. 9, the opaque border region 35 partially borders the transparent window region 30 along an edge 32 near the top wall 25 and along an edge 33 nearer to the bottom wall 26. In the example of FIG. 9, the housing portion 12 includes a C-shaped opaque, paperboard insert 14 which partially obscures the front wall 20, the back wall 21, the top wall 25, and the bottom wall 26, such that the insert defines the transparent window region 30. This example also includes transparent windows in side walls 23 and 24. The transparent windows in the side walls 23 and 24 are each unobscured and allow ready visibility into the contents of the package 10.

Figure 3:
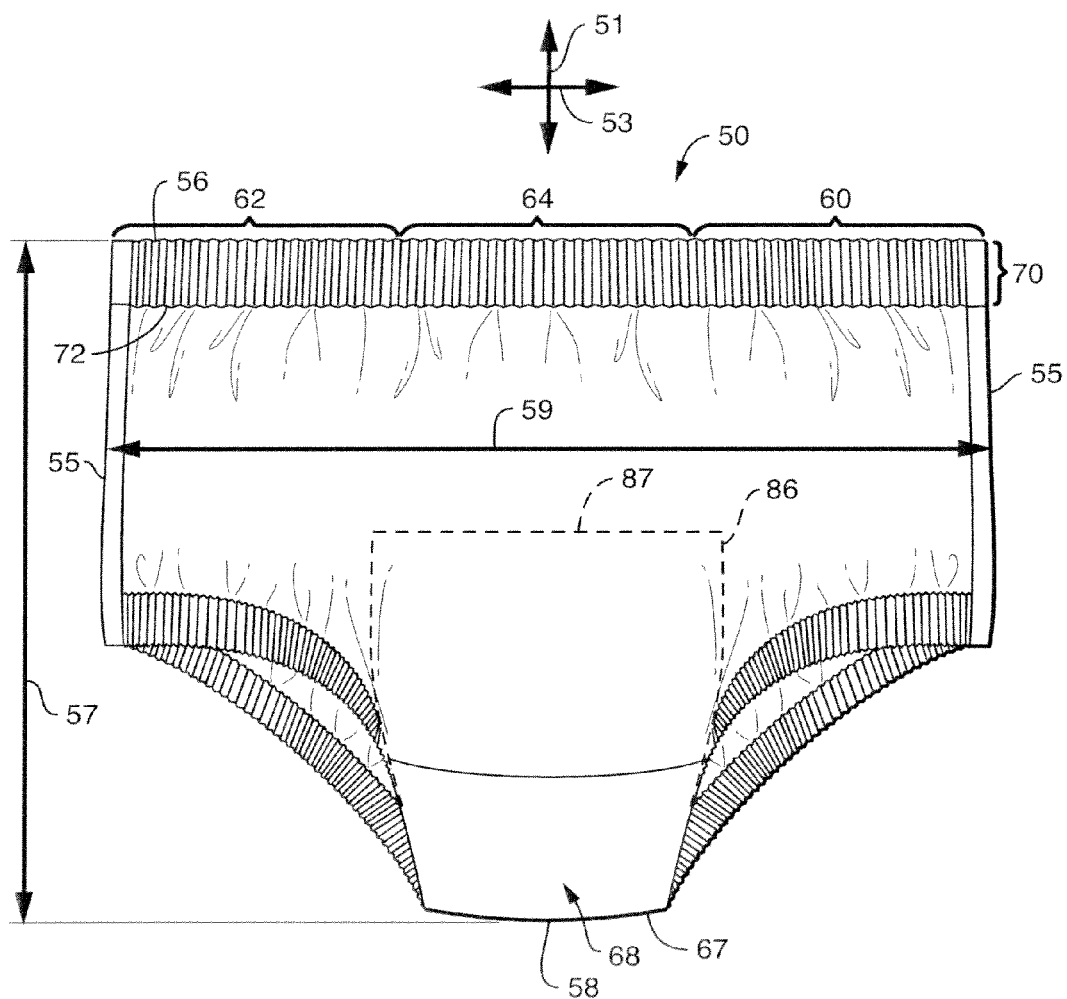
FIG. 3 representatively illustrates a front plan view of the disposable absorbent pant of FIG. 2, shown in a relaxed and laid-flat condition.

The package 10 further includes a plurality of disposable absorbent pants disposed within the housing portion 12. Each pant 50 defines a waist opening 52, two leg openings 54, a waist end 56, and a crotch end 58. In particular embodiments, each pant include two side seams 55 which join the front portion of the pant to the back portion. Each pant defines a longitudinal direction 51 that extends from the waist end 56 to the crotch end 58, and each pant defines a transverse direction 53 that is perpendicular to the longitudinal direction 51. Each pant 50 defines an assembled length 57 which extends in the longitudinal direction 51 from the waist end 56 to the crotch end 58. (If the front waistband portion 72 and the back waistband portion 74 are different distances from the crotch end 58, then the assembled length 57 of the pant is the longer of the two distances.) Each pant also defines a width 59 which extends in the transverse direction 53 from one side seam 55 to the other side seam 55. The length 57 and width 59 for purposes herein are measured when the pant is in a fully assembled (side seams intact), relaxed condition, such as that depicted in FIG. 3. The length 57 is measured at the longitudinal centerline of the pant 50, and the width 59 is measured at the longitudinal midpoint of each side seam 55. Each pant further defines a first side portion 60, a second side portion 62, and a center portion 64 positioned transversely between the first side portion 60 and the second side portion 62. The first side portion 60 extends 20% to 40% of the transverse width 59 of the pant 50 in an assembled, laid-flat, relaxed condition. The second side portion 62 extends 20% to 40% of the transverse width 59 of the pant 50 in an assembled, laid-flat, relaxed condition. The center portion 64 extends approximately 20% to 50% of the width 59 of the pant 50 in an assembled, laid-flat, relaxed condition. In particular embodiments, the first side portion 60, the second side portion 62, and the center portion 64 each extend approximately one-third of the width 59 of the pant 50 in a laid-flat, relaxed condition, as is generally representatively illustrated in FIG. 3.

In particular embodiments, each pant includes a front panel 71, a back panel 73, and a crotch panel 75. The panels 71,73, 75 may be integral with each other, or may comprise separate components attached to one another. In particular embodiments, the front and back panels 71,73 comprise elastomeric materials, such as elastomeric film laminates, elastomeric stranded laminates, elastomeric net or mesh laminates, or the like. In one example, the front and back panels 71,73 each comprise an elastomeric film sandwiched between two polyolefin-based, cloth-like, nonwoven substrates.

Each pant 50 further defines a waistband region 70 which abuts the waist end 56. The waistband region 70 extends in the transverse direction 53 and at least partially encircles the waist opening 52. Each waistband region 70 comprises a front waistband portion 72 and a back waistband portion 74. Each waistband portion 72,74 extends between the side seams 55. The front waistband portion 72 is adapted to contact the front half of a wearer's waist when donned, and the back waistband portion 74 is adapted to contact to the back half of a wearer's waist when donned. The waistband portions 72,74 can be integral with the front and back panels 71,73, or can be separate components that are attached to the front and back panels 71,73. For example, the front waistband portion 72 can constitute the region of the front panel 71 that is within 25 centimeters, or within 35 centimeters, of the front waist edge 76, and the back waistband portion 74 can constitute the region of the back panel 73 that is within 25 centimeters, or within 35 centimeters, of the back waist edge 77. Alternatively, the front waistband portion 72 can comprise a folded-over portion of the front panel 71, and/or the back waistband portion 74 can comprise a folded-over portion of the back panel 73. In particular embodiments, a transversely extending fold line defines the front waist edge 76, and a transversely extending fold line defines the back waist edge 77. In such embodiments, the longitudinal length of the folded portion defines the boundaries of the respective waistband portion. Desirably, one or more elastic strands are disposed within one or both folded-over portions. Examples of such folded-over waistband configurations are shown in U.S. Patent Application Publication 2008/0134487 to Hartono, which is incorporated by reference to the extent consistent herewith. Alternatively, the front waistband portion 72 can comprise a separate elastomeric component or assembly affixed to the front panel 71, and/or the back waistband portion 74 can comprise a separate elastomeric component or assembly affixed to the back panel 73, as representatively illustrated in FIG. 1. Each pant also defines a crotch region 68 which abuts the crotch end 58.

Each pant also desirably includes an absorbent composite 80 generally disposed in the center portion 64 and in the crotch region 68. In particular embodiments, the absorbent composite 80 can but need not include a liquid-impermeable garment-side backsheet 82, a liquid-permeable body-side topsheet 84, and a fluid-absorbing core 86 comprised of fluff pulp and/or superabsorbent polymer sandwiched between the backsheet 82 and the topsheet 84. The absorbent core 86 has a front edge 87, a back edge 88 spaced from the front edge in the longitudinal direction, and two side edges 89 which extend from the front edge 87 to the back edge 89. The absorbent core 86 may be rectangular, hour-glass, oval, trapezoid, or other suitable shape. Due to the additional bulk introduced by an absorbent core 86, the crotch region 68 of a pant 50 that includes an absorbent core 86 is generally thicker than the waistband region 70 of such pant. Examples of disposable absorbent pants having certain aspects suitable for incorporation into particular embodiments of the present invention include those disclosed in U.S. Pat. No. 5,745,922 issued May 5, 1998 to Rajala et al., U.S. Pat. No. 6,240,569 issued Jun. 5, 2001 to Van Gompel et al., U.S. Pat. No. 6,702,798 issued Mar. 9, 2004 to Christoffel et al., and U.S. Pat. No. 7,604,624 issued Oct. 20, 2009 to Veith et al., the contents of each of which is hereby incorporated by reference to the extent consistent herewith. Note that the disposable absorbent pants could be provide in a permanently "closed" (i.e., pull-on style) configuration, a releasably and refastenably "closed" configuration, or an "open" (i.e., non-prefastened) configuration—any of which could be used in conjunction with the various embodiments of the present invention.

Figure 4A:
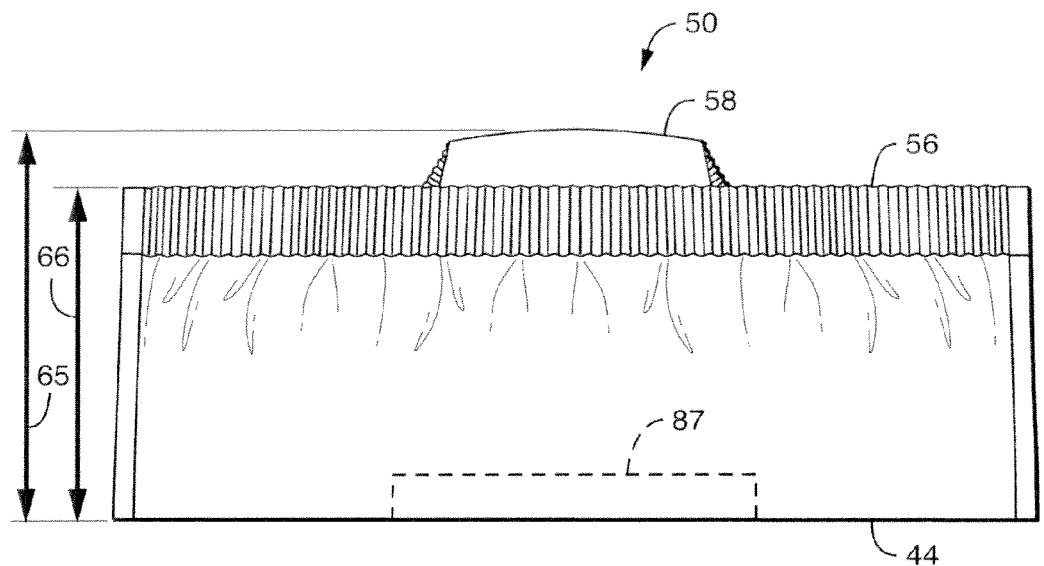
FIG. 4A representatively illustrates a front plan view of an intermediate folded configuration of the disposable absorbent pant of FIG. 3, shown in a transversely tensioned condition, with one longitudinal fold.
Figure 4B:
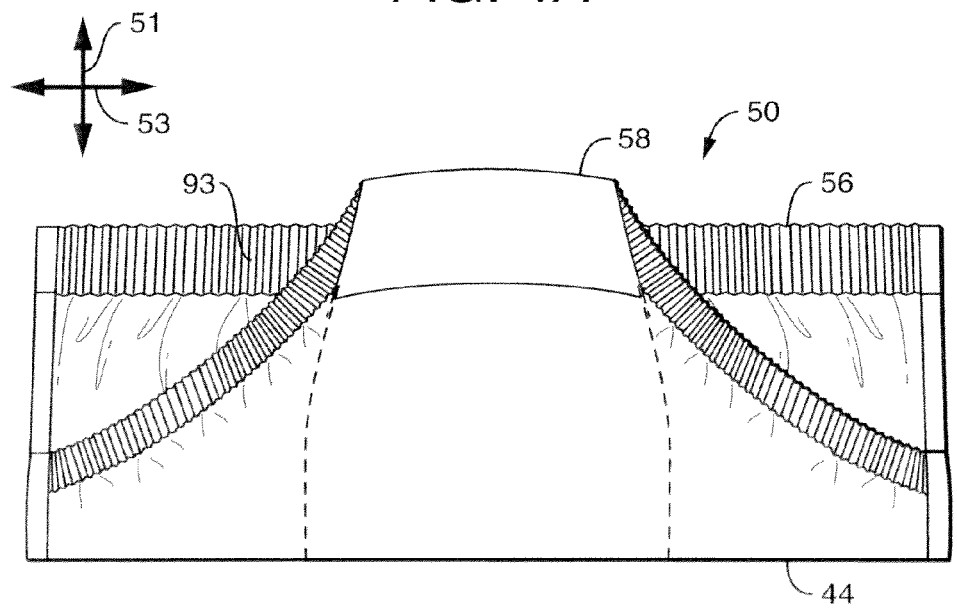
FIG. 4B representatively illustrates a back plan view of an intermediate folded configuration of the disposable absorbent pant of FIG. 3, shown in a transversely tensioned condition, with one longitudinal fold.
Figure 4C:
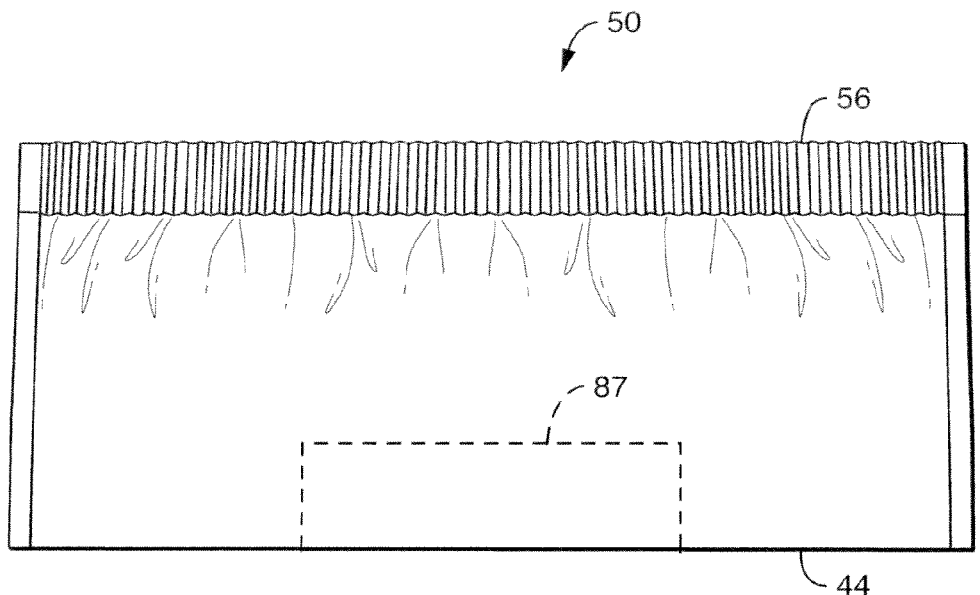
FIG. 4C representatively illustrates a front plan view of an alternative intermediate folded configuration of the disposable absorbent pant of FIG. 3, shown in a transversely tensioned condition, with one longitudinal fold.
Figure 4D:
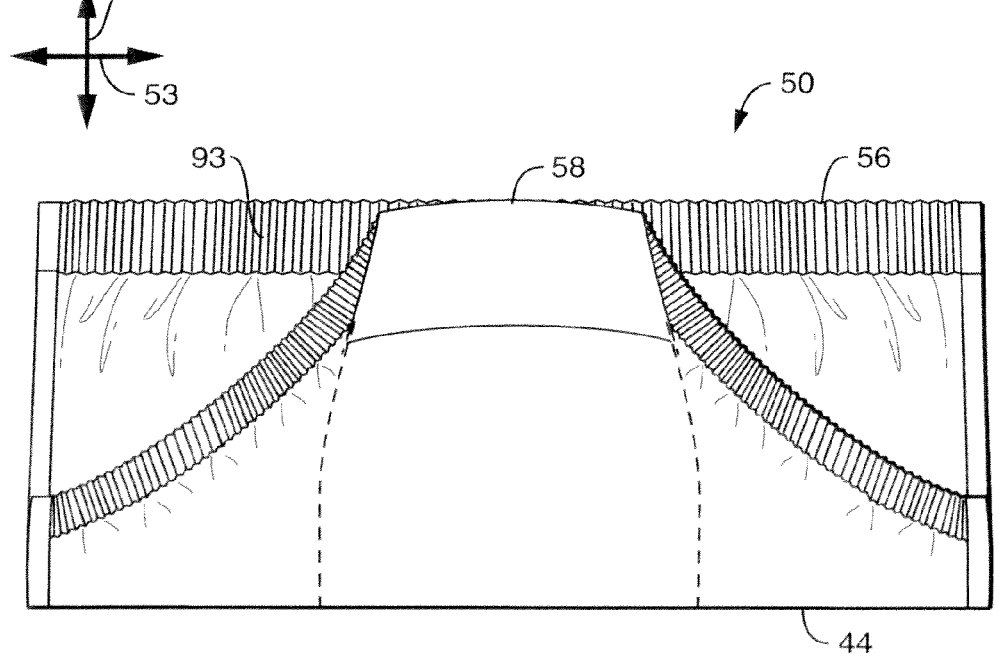
FIG. 4D representatively illustrates a back plan view of an alternative intermediate folded configuration of the disposable absorbent pant of FIG. 3, shown in a transversely tensioned condition, with one longitudinal fold.
Figure 5A:
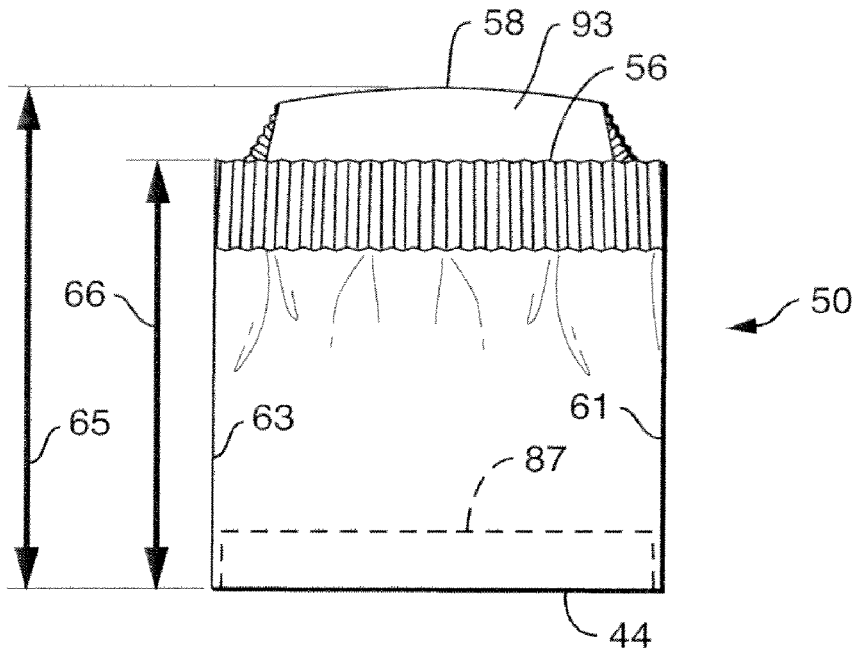
FIG. 5A representatively illustrates a front plan view of a fully folded configuration of the disposable absorbent pant of FIG. 3, with both side portions folded under the center portion.
Figure 5B:
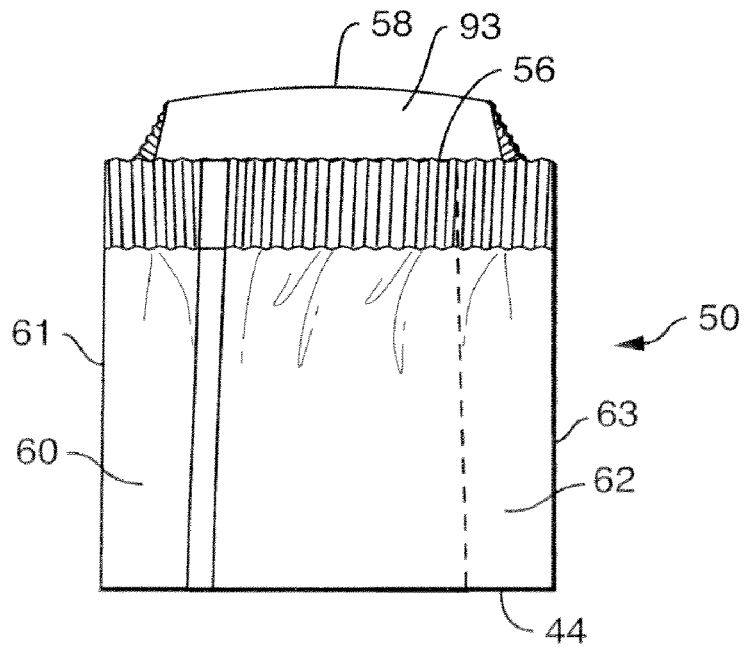
FIG. 5B representatively illustrates a back plan view of a fully folded configuration of the disposable absorbent pant of FIG. 3, with both side portions folded over the center portion.
Figure 5C:
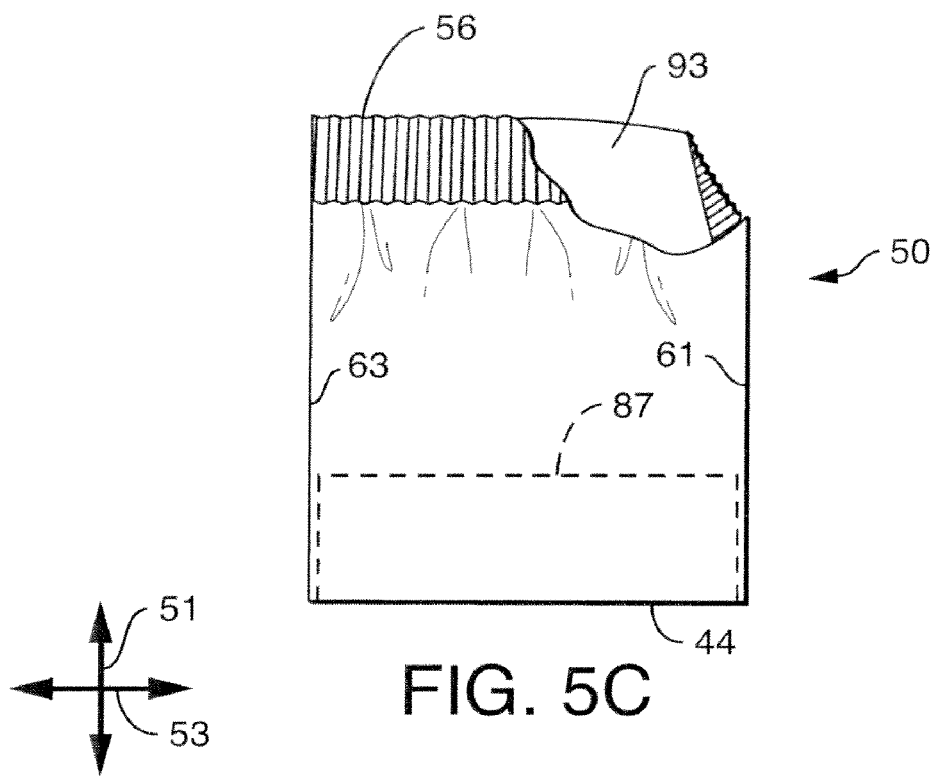
FIG. 5C representatively illustrates a front plan view of an alternative fully folded configuration of the disposable absorbent pant of FIG. 3, with both side portions folded under the center portion, and with portions cut away to show underlying features.
Figure 5D:
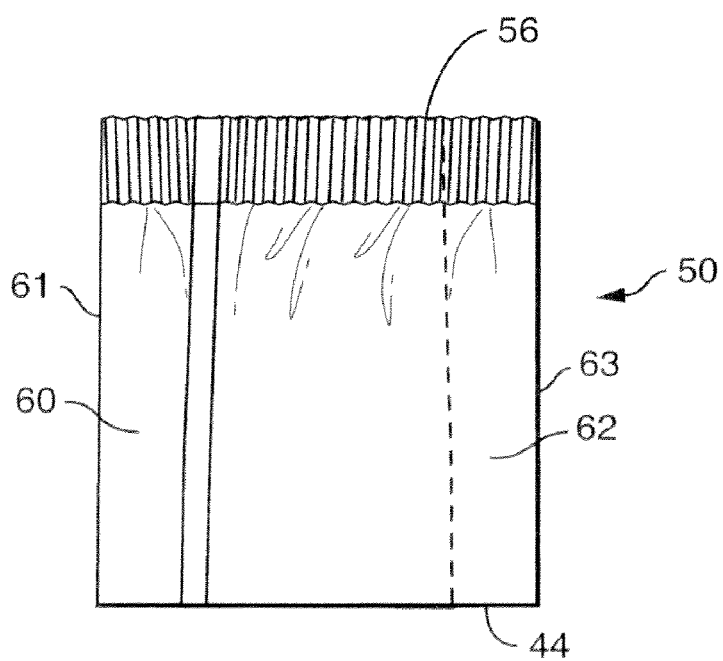
FIG. 5D representatively illustrates a back plan view of an alternative fully folded configuration of the disposable absorbent pant of FIG. 3, with both side portions folded over the center portion.
Figure 6A:
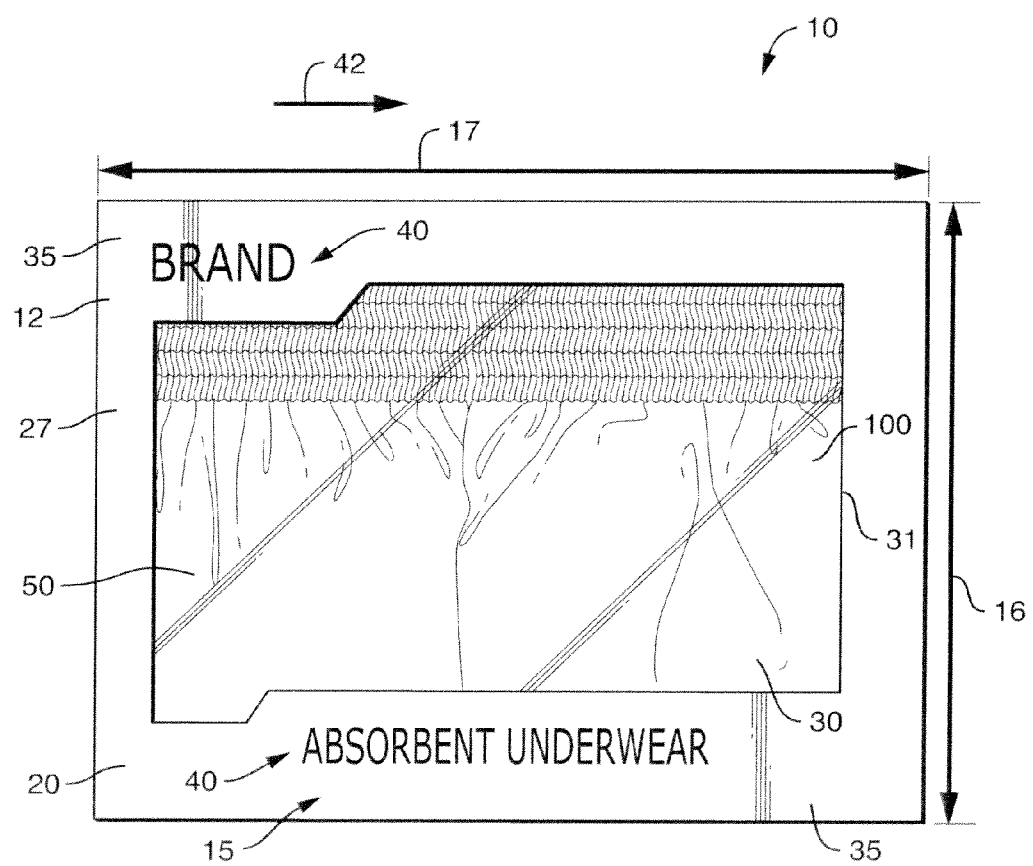
FIG. 6A representatively illustrates a front plan view of one embodiment of the package of the present invention.
Figure 6B:
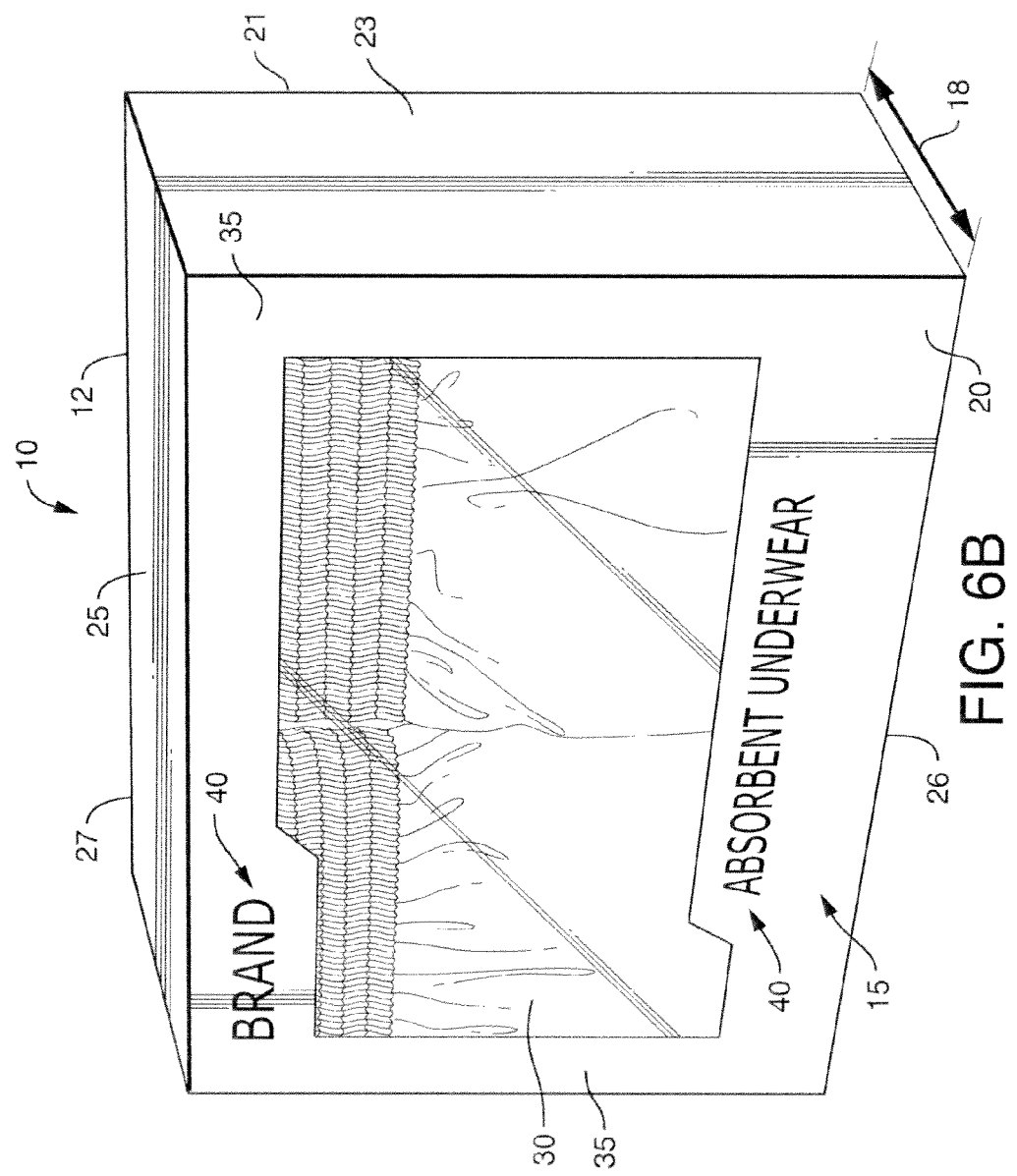
FIG. 6B representatively illustrates a perspective view of the embodiment of FIG. 6A.

In particular embodiments, one, more than one, or all of the plurality of pants 50 is/are folded at least once in the longitudinal direction 51. In particular embodiments, as representatively illustrated in FIG. 4, the pant 50 is folded at first longitudinal fold line 44 so as to position the crotch end 58 in close proximity to the waist end 56. The crotch end 58 can be positioned to be flush with the waist end 56, as representatively illustrated in FIGS. 4C-D. Alternatively, the crotch end 58 can be positioned to not be flush with the waist end 56, such that the waist end 56 and the crotch end 58 are different distances from the fold line 44. For example, as depicted in FIGS. 4A-B, the pant 50 may be folded such that distance 65 between the crotch end 58 and the fold line 44 is greater than the distance 66 between the waist end 56 and the fold line 44. The first longitudinal fold line 44 can be, but need not be, longitudinally near the front edge 87 of the absorbent core 86, as is the case in the embodiment of FIG. 4A. When a pant 50 is folded so as to position the crotch end 58 in close proximity to the waist end 56, the pant may be folded such that the crotch region 68 directly contacts the front waistband portion 72, or such that the crotch region 68 directly contacts the back waistband portion 74. In particular embodiments, such as that representatively illustrated in FIGS. 5A-D and 10A-B, the pant 50 is folded such that the crotch region 68 at least partially directly contacts the back waistband portion 74. In such an embodiment, the garment-side surface 93 of the crotch region 68 of the pant 50 directly contacts the garment side-surface 93 of the back waistband portion 74 of the waistband region 70.

In particular embodiments, one, more than one, or, most preferably, all of the plurality of pants 50 is/are folded at least once, and preferably twice, in the transverse direction 53. In particular, as representatively illustrated in FIGS. 5A-D, the first side portion 60 and the second side portion 62 of each pant 50 are folded over/under the center portion 64. In particular, the first side portion 60 is shown folded over the center portion 64 at a first transverse fold line 61, and the second side portion 62 is shown folded over both the center portion 64 and the first side portion 60 at a second transverse fold line 63. In this way, the pant 50 is folded twice in the transverse direction 53. In alternative embodiments, the first side portion 60 and the second side portion 62 can both be tucked within—as opposed to folded over/under—the center portion 64 (not shown). Representative examples of disposable pants having side portions tucked into a center portion and methods to so tuck are disclosed in U.S. Pat. No. 6,723,035 issued Apr. 20, 2004 to Franklin et al., and the entirety of the portions of the '035 patent that relate to tucked side portions or tucked panels are hereby incorporated by reference to the extent consistent herewith.

Note that for the purposes of the present disclosure, the crotch fold 67 of the pant 50 is ignored for purposes of counting the number of times that the pant is folded in the longitudinal direction 51. For example, for purposes of the present disclosure, the pants 50 depicted in FIGS. 4A-D are considered to be folded just once in the longitudinal direction 51 (namely, at first longitudinal fold line 44). Similarly, for purposes of the present disclosure, the pants 50 depicted in FIGS. 5A-D are considered to be folded twice in the transverse direction 53 (namely, at transverse fold lines 61 and 63), but just once in the longitudinal direction 51 (namely, at first longitudinal fold line 44).

In particular embodiments, the pant 50 is folded at least once in the longitudinal direction 51 so as to position the crotch end 58 in close proximity to the waist end 56 as described above before the pant 50 is folded in the transverse direction 53 as described above. For example, as representatively illustrated in the embodiment of FIGS. 4 and 5, the pant 50 is first folded at longitudinal fold line 44, is thereafter folded at first transverse fold line 61, and is finally folded at second transverse fold line 63. In the folded configuration depicted in FIG. 5, the majority of the crotch region 68 is at least partially sandwiched between the first side portion 60 and the center portion 64. In particular embodiments, such as that representatively illustrated in FIG. 5, both the front waistband portion 72 and the back waistband portion 74 of the waistband region 70 are wrapped around the crotch region 68. In such embodiments, it can be desirable to have the waistband region 70 of the pant in a tensioned condition. Having the waistband region 70 in a tensioned or partially taut condition can assist in highlighting the "real underwear"-like properties of the pant to a consumer viewing the pant through the transparent window region 30, as further detailed below. In particular embodiments, such as those in which the waistband region 70 is wrapped around the crotch region 68, the first side portion 60 directly contacts the second side portion 62 (see, for example, FIGS. 5B and 5D).

Referring to FIGS. 6-8 and 11, in particular embodiments at least one pant 50, such as at least two pants, of the plurality of disposable absorbent pants is positioned within the housing portion 12 such that the longitudinal direction 51 of the at least one pant 50 extends in the height dimension 16 of the housing portion 12, and such that at least a portion of the waistband region 70 of the pant 50 is visible through the transparent window region 30, and such that the crotch end 58 of the pant 50 is visually obscured by the opaque border region 35. In this way, it can in certain embodiments be possible to highlight for a consumer the waistband region 70 of the absorbent pant (such as an elastic waistband) which hearkens to regular cloth underwear, but to make less apparent or to cover up those aspects of the absorbent pant that hearken to disposable bladder weakness absorbent products, such as the thicker absorbent core 86 near the crotch end 58 in the crotch region 68. For example, as discussed above in conjunction with the embodiment of FIGS. 4A-B, the pant 50 may be folded such that distance 65 between the crotch end 58 and the fold line 44 is greater than the distance 66 between the waist end 56 and the fold line 44. In particular embodiments, distance 65 between the crotch end 58 and the fold line 44 exceeds the distance 66 between the waist end 56 and the fold line 44 by at least 1 centimeter, more particularly by at least 2 centimeters, and still more particularly by between 2 and 5 centimeters. Without intending to be limiting, the present inventors have discovered that these particular dimensional relationships can in particular embodiments optimize the balance between displaying desired features of the product through the window region and concealing other regions of the product behind opaque regions. In particular embodiments, such as those of FIGS. 6, 7, and 11, the waist end 56 is closer to the top wall 25 of the housing portion 12 than to the bottom wall 26 of the housing portion 12, and the top wall 25 of the housing portion 12 is closer to the crotch end 58 than to the waist end 56. In particular embodiments, the crotch region 68 of the pant 50 is entirely obscured by the opaque border region 35.

Figure 7A:
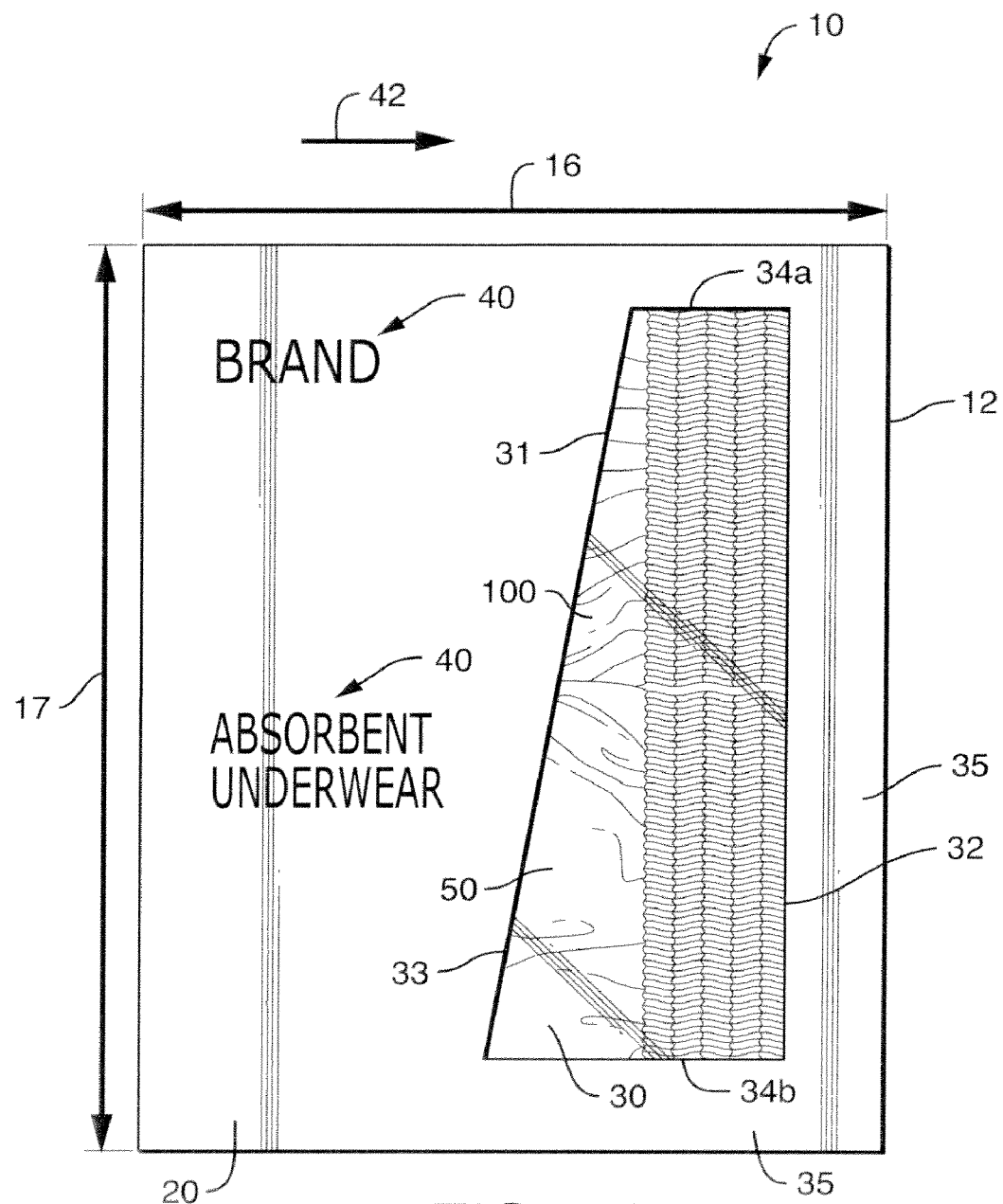
FIG. 7A representatively illustrates a front plan view of another embodiment of the package of the present invention.
Figure 7B:
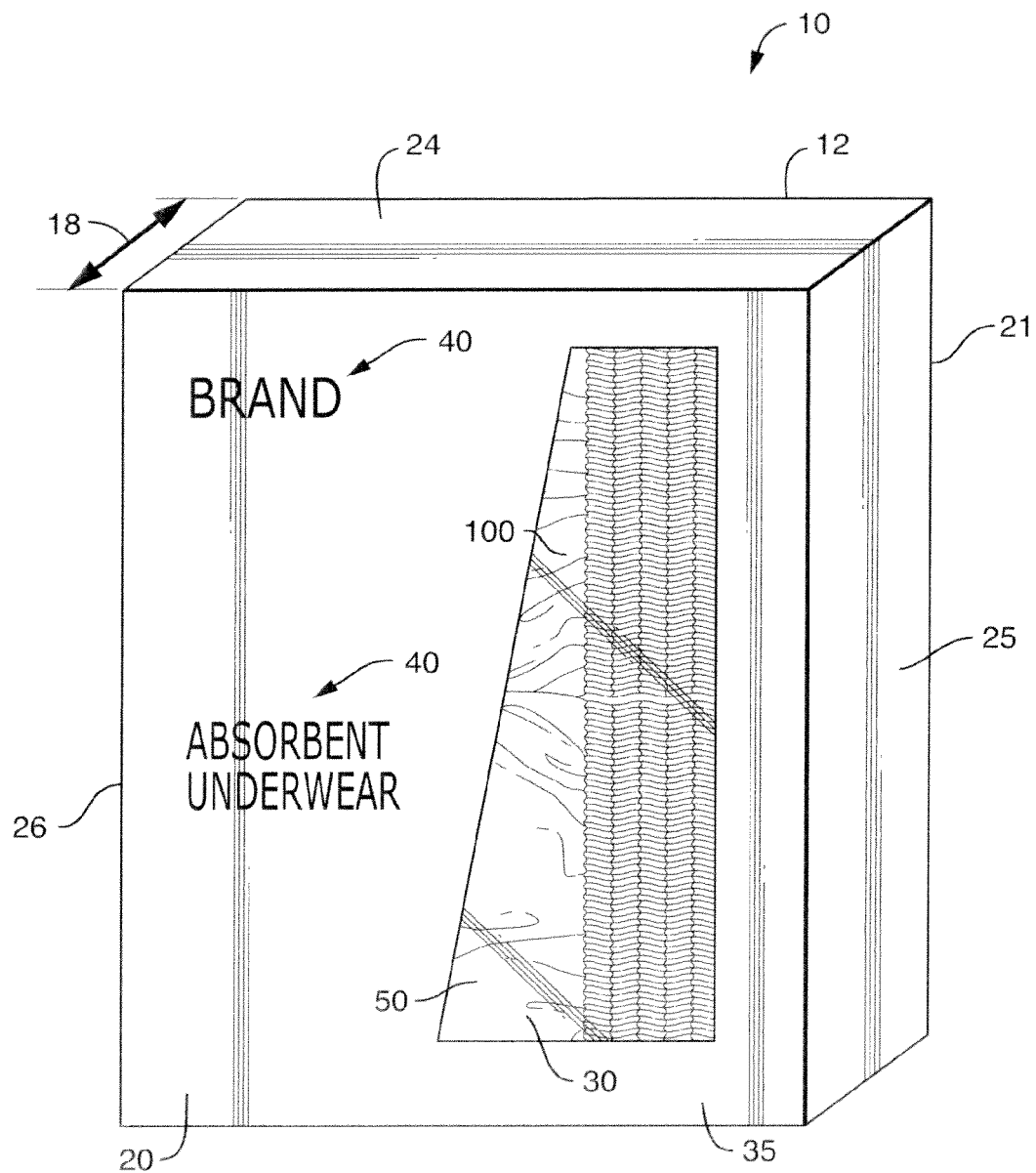
FIG. 7B representatively illustrates a perspective view of the embodiment of FIG. 7A.
Figure 7C:
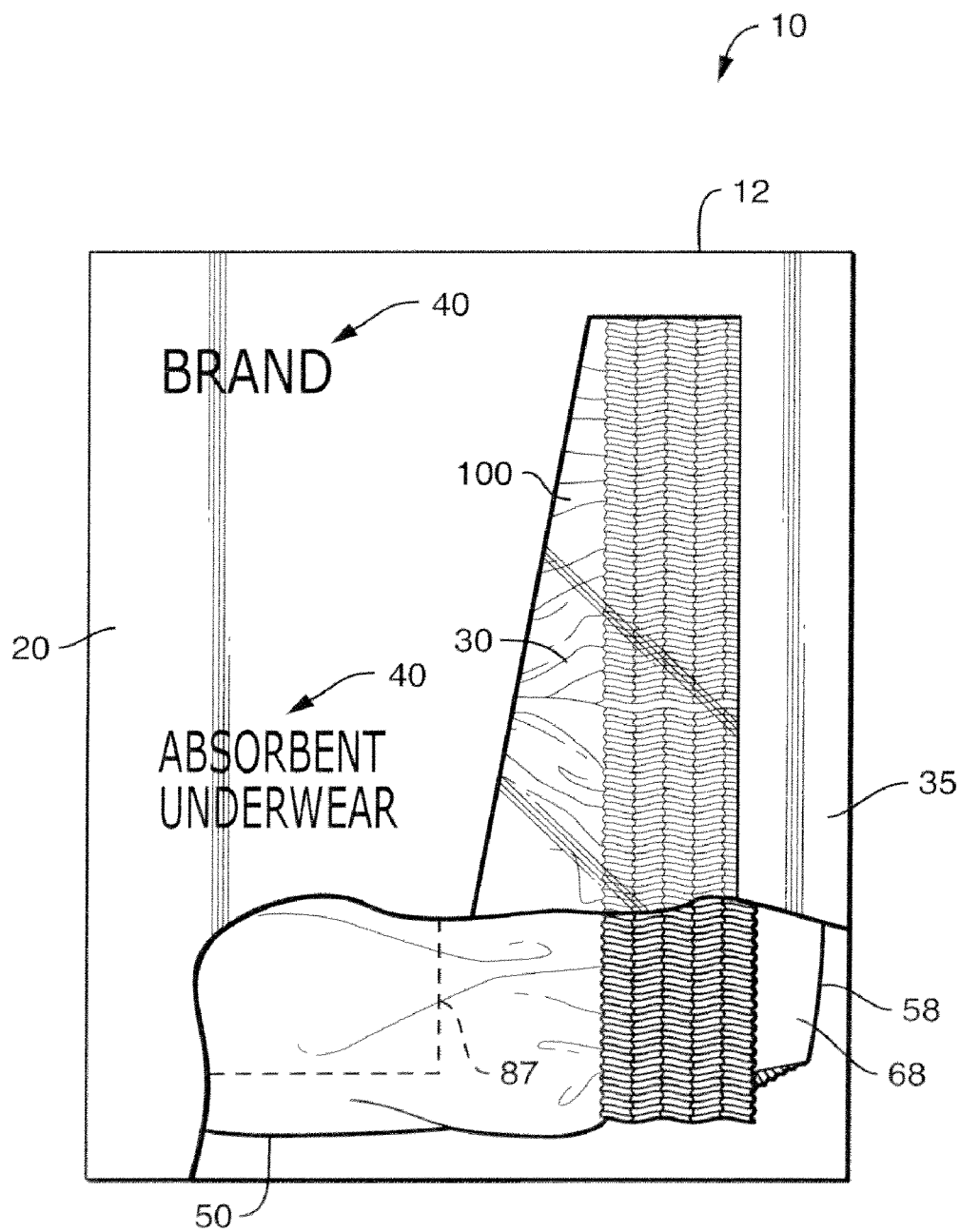
FIG. 7C is the same as FIG. 7B but with portions cut away to show underlying features.

Referring to FIGS. 7a-7c, in particular embodiments at least one pant 50, such as at least two pants, of the plurality of disposable absorbent pants is positioned within the housing portion 12 such that the longitudinal direction 51 of the at least one pant 50 extends in the height dimension 16 of the housing portion 12, and such that at least a portion of the waistband region 70 of the pant 50 is visible through the transparent window region 30 and such that the front edge 87 of the absorbent core 86 of the pant is obscured by the opaque border region 35. In this way, it can be possible to highlight for a consumer the waistband region 70 of the absorbent pant (such as an elastic waistband) which hearkens to regular cloth underwear, but to make less apparent or to cover up those aspects of the absorbent pant that hearken to disposable bladder control absorbent products, such as the relatively bulky absorbent core near the front edge 87 of the absorbent core. In FIGS. 7a and 7b, the front edge of the absorbent core of both the first pant 50 and the second pant 100 is hidden from view by the opaque border region 35. FIG. 7c shows the package of FIGS. 7a and 7b but with portions of the housing portion 12 cut away to reveal the front edge 87 of the absorbent core 86 of the first pant 50, as well as to reveal the crotch end 58 of the first pant 50. In particular embodiments, not only is the front edge 87 of the absorbent core 86 obscured by the opaque border region 35, but the entirety of the absorbent core 86 is obscured by the opaque border region 35. Stated another way, in such embodiments, no portion of the absorbent core 86 is visible through the transparent window region 30 of the package 10.

Figure 10A:
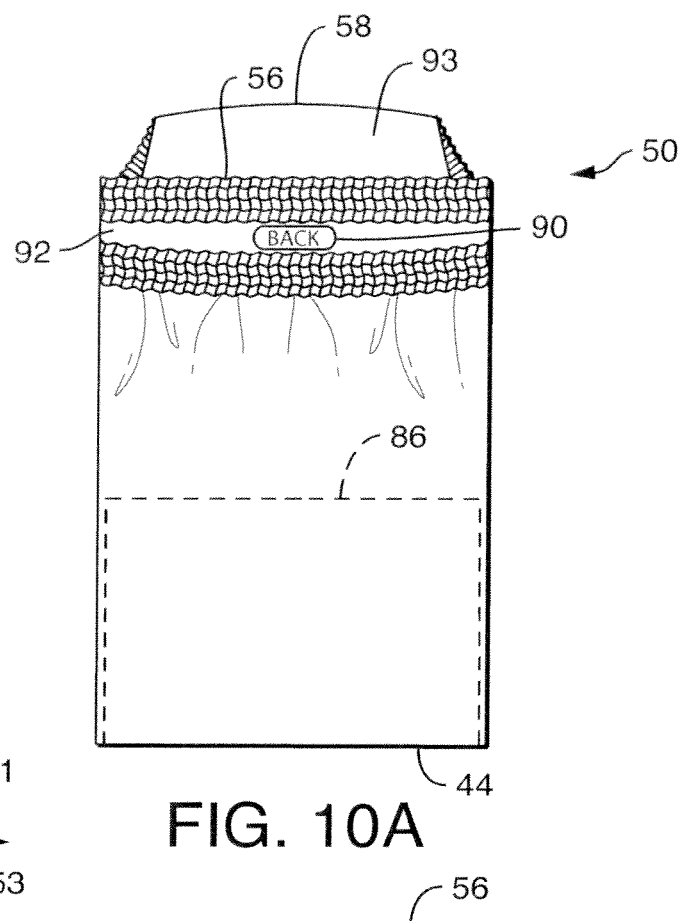
FIG. 10A representatively illustrates a front plan view of an alternative fully folded configuration of a disposable absorbent pant similar to the pant depicted in FIG. 3, with both side portions folded under the center portion.
Figure 10B:
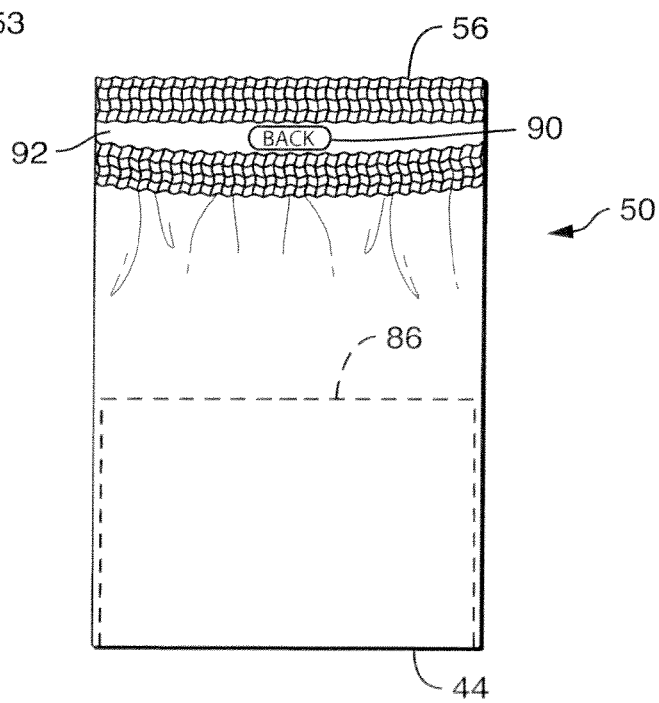
FIG. 10B representatively illustrates a front plan view of another alternative fully folded configuration of a disposable absorbent pant similar to the pant depicted in FIG. 3, with both side portions folded under the center portion.
Figure 11:
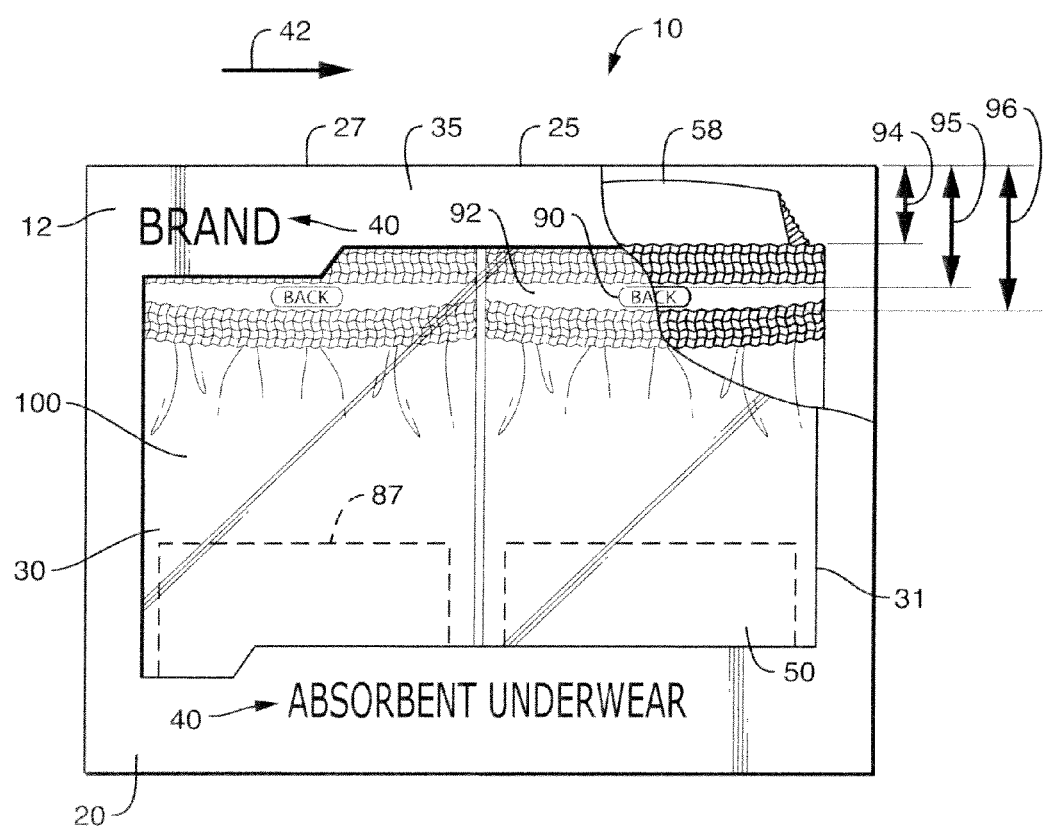
FIG. 11 representatively illustrates a front plan view of another embodiment of the package of the present invention.

Referring to FIGS. 10-11, in particular embodiments, at least one of plurality of pants in the package, and preferably all of the pants in the package, include a back-label indicator 90 disposed on the back panel 73 of the pant 50. A back-label indicator can provide at least two benefits in particular embodiments—namely, denoting which portion of the pant is the back of the pant to the wearer, and helping to make the pant more closely resemble "regular" cloth underwear. In particular embodiments, such as those representatively illustrated in FIGS. 10 and 11, the back-label indicator 90 is disposed on a bodyside layer of the pant, and preferably on the bodyside surface 92 of the pant. Preferably, the back-label indicator is positioned so as to be in close proximity to the back waistband portion 74, such as on the back waistband portion, or, as representatively illustrated in FIGS. 10-11, just below the waistband portion 74. Note that the back-label indicator 90 could be disposed on any surface of any layer, so long as the back-label indicator 90 is visible when viewing the body-side surface or the garment-side surface of the pant.

In particular embodiments, such as that representatively illustrated in FIG. 11, the back-label indicator 90 of one pant, of two pants, of three pants, of four pants, or of more than four pants, are visible through the transparent window region 30. In the embodiment of FIG. 11, the two pants 50, 100 that are visible through the transparent window region 30 are folded and positioned as shown in FIG. 10A so as to make the back-label indicator 90 visible when viewing the pant through the window region 30. In particular embodiments, such as that representatively illustrated in FIG. 11, the back waistband portion 74 is spaced a first distance 94 from the top wall 25, the back-label indicator 90 is spaced a second distance 95 from the top wall 25, and the front waistband portion 72 is spaced a third distance 96 from the top wall 25. The first distance 94 is less than the second distance 95, and the second distance 95 is less than the third distance 96. Each distance is measured at the longitudinal centerline of the respective pant. In this way, the back-label indicator is visible through the window region, as is one or both of the front and back waistband portions 72/74.

Desirably, printed text 40 is disposed on or near the front wall 20. For example, the printed text 40 can be printed on an outer surface 15 of the housing portion 12, or on a surface of an insert 14. The printed text 40 extends in a reading direction 42. "Reading direction" means the direction in which the printed text reads, such as left-to-right in languages that employ the Roman alphabet. In particular embodiments, such as those representatively illustrated in FIGS. 6, 8, and 11, the printed text 40 is oriented such that the reading direction 42 extends in the width dimension 17. In such embodiments, the reading direction 42 is perpendicular to both the height dimension 16 as well as to the longitudinal direction 51 of each pant 50 within the package 10. In other embodiments, such as those representatively illustrated in FIGS. 7 and 9, the printed text 40 is oriented such that the reading direction 42 extends in the height dimension 16. In such embodiments, the reading direction 42 is perpendicular to both the width dimension 17 as well as to the transverse direction 53 of each pant 50 within the package 10.

Referring to FIG. 9, in particular embodiments of the package 10, the plurality of pants includes a first row 102 of pants stacked behind a first pant 50. The first row 102 extends in the depth dimension 18 between the first pant 50 and the back wall 21. One or more of the pants stacked behind the first pant 50 may have any of the features described above. Additionally, in particular embodiments of the package 10, a second pant 100 is positioned within the housing portion adjacent the first pant 50. As with the first pant 50, the second pant 100 may be positioned within the housing portion 12 such that the longitudinal direction 51 of the second pant 100 extends in the height dimension 16, and such that at least a portion of the waistband region 70 of the second pant 100 is visible through the transparent window region 30. In particular embodiments, the crotch end 58 of the second pant 100 is obscured by the opaque border region 35, as is representatively illustrated in FIGS. 7A-C. Additionally or in the alternative, the front edge of the absorbent core of the second pant 100 is obscured by the opaque border region 35. In particular embodiments, the second pant 100 is positioned alongside the first pant 50 in the width dimension 17 of the housing portion 12. In such embodiments, it is desirable to also include a second row of pants stacked behind the second pant 100, such that the second row, like the first row 102, extends in the depth dimension 18 between the second pant 100 and the back wall 21. In an alternative embodiment (not shown), in which the second pant 100 is positioned alongside the first pant in the width dimension 17, a single row of pants may extend in a stack from the first side wall 23 to the second side wall 24, such that the transverse axes of both the first and second pants 50,100 are disposed at a generally right angle to the transverse axes of each of the pants in the stack that extends in the width dimension 17 from side wall 23 to side wall 24.

Figure 8:
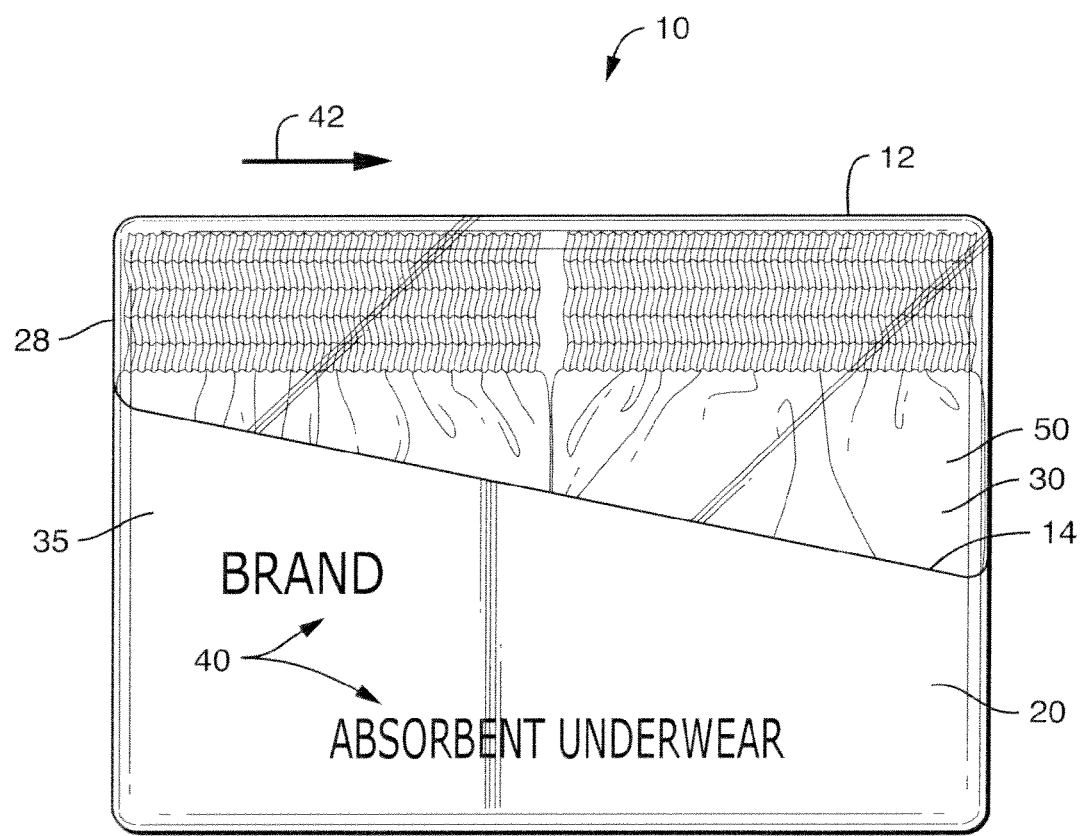
FIG. 8 representatively illustrates a front plan view of another embodiment of the package of the present invention.
Figure 9:
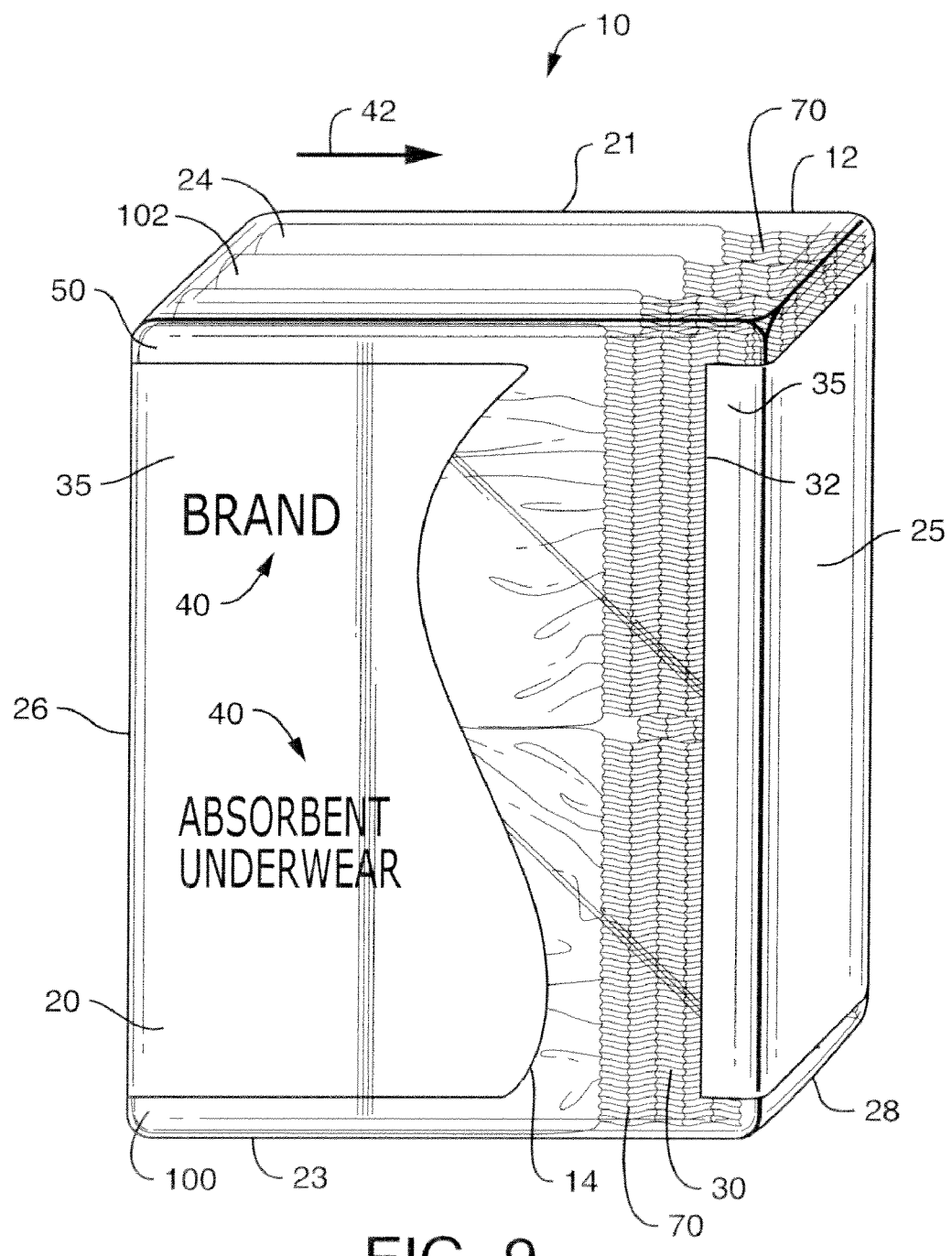
FIG. 9 representatively illustrates a perspective view of another embodiment of the package of the present invention.

In particular embodiments, such as those representatively illustrated in FIGS. 7-9, the transparent window region 30 is configured to reveal different portions, different amounts, or different areas of the first pant 50 and the adjacent second pant 100. For example, in the embodiment of FIG. 7, the window is configured to show primarily the waistband region 70 but relatively little of the rest of the front panel 71 of the second pant 100. However, the window region 30 is at the same time configured to show the waistband region 70 as well as a relatively greater area of the front panel 71 of the first pant 50. In this way, the window region 30 can draw the viewer's attention to the waistband region 70 in one product, and at the same time draw attention also to the cloth-like attributes of the front panel 71 in the adjacent product. One example of a way to accomplish this is to shape the window such that the first window side edge 34a is shorter that the second window side edge 34b. In this way, one of or both the top edge 32 and the bottom edge 33 may be curved, or sloped as shown in FIG. 7. An alternative approach is depicted in FIG. 9, where the lower border region is shaped so as to cover a greater amount of the second pant 100 than of the first pant 50. In particular embodiments, the border region 35 and window region 30 are configured so that more, such as at least 20% more, of the first pant 50 is visible (as measured by a plan view footprint) through the window region 30, relative to the amount of the second pant 100 that is visible through the window region 30.

It will be appreciated that details of the foregoing embodiments, given for purposes of illustration, are not to be construed as limiting the scope of this invention. Although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A package of folded disposable absorbent pants, the package comprising:
   a housing portion which defines a height dimension, a width dimension, and a depth dimension, the housing portion comprising a front wall and a back wall, each of which extends along the width and height dimensions, the front wall being spaced from the back wall in the depth dimension, wherein the front wall comprises a transparent window region and an opaque border region;
   a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion, each pant further defining a waistband region which abuts the waist end and which extends in the transverse direction to at least partially encircle the waist opening, each waistband region comprising a front waistband portion and a back waistband portion, each pant further defining a crotch region which abuts the crotch end;
   wherein each of the plurality of pants is folded at least once in the longitudinal direction so as to position the crotch end in close proximity to the waist end, and further wherein each of the plurality of pants is folded twice in the transverse direction such that the first and second side portions of each pant are folded over the respective center portion;
   wherein at least a first pant of the plurality of disposable absorbent pants is positioned within the housing portion such that the longitudinal direction of the first pant extends in the height dimension, and such that at least a portion of the waistband region of the first pant is visible through the transparent window region and such that an entirety of the crotch end of the first pant is obscured by the opaque border region,
   wherein the crotch region of the first pant is at least partially sandwiched between the first side portion of the first pant and the center portion of the first pant.

2. The package of claim 1, wherein the housing portion comprises a carton, and wherein the opaque border region comprises paperboard.

3. The package of claim 1, wherein the housing portion comprises a plastic bag, wherein the transparent window region is defined by a transparent portion of the bag and wherein the opaque border region is defined by printed graphics on the bag.

4. The package of claim 1, wherein the housing portion comprises a plastic bag, wherein the transparent window region is defined by a transparent portion of the bag and wherein the opaque border region is defined by a paperboard insert positioned within the housing portion.

5. The package of claim 1, wherein the crotch region of the first pant at least partially directly contacts the back waistband portion of the first pant.

6. The package of claim 1, wherein the front wall comprises printed text extending in a reading direction, wherein the reading direction extends in the width dimension.

7. A package of folded disposable absorbent pants, the package comprising:
   a housing portion which defines a height dimension, a width dimension, and a depth dimension, the housing portion comprising a front wall and a back wall, each of which extends along the width and height dimensions, the front wall being spaced from the back wall in the depth dimension, wherein the front wall comprises a transparent window region and an opaque border region;
   a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion, each pant further defining a waistband region which abuts the waist end and which extends in the transverse direction to at least partially encircle the waist opening, each waistband region comprising a front waistband portion and a back waistband portion, each pant further defining a crotch region which abuts the crotch end;
   wherein each of the plurality of pants is folded at least once in the longitudinal direction so as to position the crotch end in close proximity to the waist end, and further wherein each of the plurality of pants is folded twice in the transverse direction such that the first and second side portions of each pant are folded over the respective center portion;
   wherein at least a first pant of the plurality of disposable absorbent pants is positioned within the housing portion such that the longitudinal direction of the first pant extends in the height dimension, and such that at least a portion of the waistband region of the first pant is visible through the transparent window region and such that an entirety of the crotch end of the first pant is obscured by the opaque border region, wherein the first pant is folded at least once in the longitudinal direction so as to position the crotch end in close proximity to the waist end before the first pant is folded in the transverse direction.

8. A package of folded disposable absorbent pants, the package comprising:

a housing portion which defines a height dimension, a width dimension, and a depth dimension, the housing portion comprising a front wall and a back wall, each of which extends along the width and height dimensions, the front wall being spaced from the back wall in the depth dimension, wherein the front wall comprises a transparent window region and an opaque border region;

a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion, each pant further defining a waistband region which abuts the waist end and which extends in the transverse direction to at least partially encircle the waist opening, each waistband region comprising a front waistband portion and a back waistband portion, each pant further defining a crotch region which abuts the crotch end;

wherein each of the plurality of pants is folded at least once in the longitudinal direction so as to position the crotch end in close proximity to the waist end, and further wherein each of the plurality of pants is folded twice in the transverse direction such that the first and second side portions of each pant are folded over the respective center portion;

wherein at least a first pant of the plurality of disposable absorbent pants is positioned within the housing portion such that the longitudinal direction of the first pant extends in the height dimension, and such that at least a portion of the waistband region of the first pant is visible through the transparent window region and such that an entirety of the crotch end of the first pant is obscured by the opaque border region, wherein the first pant further includes a back-label indicator disposed on a bodyside surface of the first pant in close proximity to the back waistband portion, and wherein the back-label indicator of the first pant is visible through the transparent window region.

9. A package of folded disposable absorbent pants, the package comprising:

a housing portion which defines a height dimension, a width dimension, and a depth dimension, the housing portion comprising a front wall and a back wall, each of which extends along the width and height dimensions, the front wall being spaced from the back wall in the depth dimension, wherein the front wall comprises a transparent window region and an opaque border region;

a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion, each pant further defining a waistband region which abuts the waist end and which extends in the transverse direction to at least partially encircle the waist opening, each waistband region comprising a front waistband portion and a back waistband portion, each pant further defining a crotch region which abuts the crotch end;

wherein each of the plurality of pants is folded at least once in the longitudinal direction so as to position the crotch end in close proximity to the waist end, and further wherein each of the plurality of pants is folded twice in the transverse direction such that the first and second side portions of each pant are folded over the respective center portion;

wherein at least a first pant of the plurality of disposable absorbent pants is positioned within the housing portion such that the longitudinal direction of the first pant extends in the height dimension, and such that at least a portion of the waistband region of the first pant is visible through the transparent window region and such that an entirety of the crotch end of the first pant is obscured by the opaque border region, wherein the housing portion further comprises a top wall and a bottom wall, each of which extends along the width and depth dimensions, the top wall being spaced from the bottom wall in the height dimension, wherein the waist end of the first pant is closer to the top wall than to the bottom wall, and wherein the top wall is closer to the crotch end of the first pant than to the waist end of the first pant.

10. A package of folded disposable absorbent pants, the package comprising:

a housing portion which defines a height dimension, a width dimension, and a depth dimension, the housing portion comprising a front wall and a back wall, each of which extends along the width and height dimensions, the front wall being spaced from the back wall in the depth dimension, wherein the front wall comprises a transparent window region and an opaque border region;

a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion, each pant further defining a waistband region which abuts the waist end and which extends in the transverse direction to at least partially encircle the waist opening, each waistband region comprising a front waistband portion and a back waistband portion, each pant further defining a crotch region which abuts the crotch end;

wherein each of the plurality of pants is folded at least once in the longitudinal direction so as to position the crotch end in close proximity to the waist end, and further wherein each of the plurality of pants is folded twice in the transverse direction such that the first and second side portions of each pant are folded over the respective center portion;

wherein at least a first pant of the plurality of disposable absorbent pants is positioned within the housing portion such that the longitudinal direction of the first pant extends in the height dimension, and such that at least a portion of the waistband region of the first pant is visible through the transparent window region and such that an entirety of the crotch end of the first pant is obscured by the opaque border region, wherein both the front waistband portion and the back waistband portion of the waistband region of the first pant are wrapped around the crotch region of the first pant.

11. The package of claim 10, wherein the waistband region of the first pant is in a tensioned condition.

12. The package of claim 10, wherein the first side portion directly contacts the second side portion.

13. A package of folded disposable absorbent pants, the package comprising:

a housing portion which defines a height dimension, a width dimension, and a depth dimension, the housing portion comprising a front wall and a back wall, each of which extends along the width and height dimensions, the front wall being spaced from the back wall in the depth dimension, wherein the front wall comprises a transparent window region and an opaque border region;

a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion, each pant further defining a waistband region which abuts the waist end and which extends in the transverse direction to at least partially encircle the waist opening, each waistband region comprising a front waistband portion and a back waistband portion, each pant further defining a crotch region which abuts the crotch end;

wherein each of the plurality of pants is folded at least once in the longitudinal direction so as to position the crotch end in close proximity to the waist end, and further wherein each of the plurality of pants is folded twice in the transverse direction such that the first and second side portions of each pant are folded over the respective center portion;

wherein at least a first pant of the plurality of disposable absorbent pants is positioned within the housing portion such that the longitudinal direction of the first pant extends in the height dimension, and such that at least a portion of the waistband region of the first pant is visible through the transparent window region and such that an entirety of the crotch end of the first pant is obscured by the opaque border region, wherein at least a second pant of the plurality of disposable absorbent pants is positioned within the housing portion such that the longitudinal direction of the second pant extends in the height dimension, and such that at least a portion of the waistband region of the second pant is visible through the transparent window region and such that the crotch end of the second pant is obscured by the opaque border region, the second pant being positioned alongside the first pant in the width dimension.

14. The package of claim 13, wherein the plurality of pants further comprises a first row of pants stacked behind the first pant, the first row extending in the depth dimension between the first pant and the back wall, and wherein the plurality of pants further comprises a second row of pants stacked behind the second pant, the second row extending in the depth dimension between the second pant and the back wall.

15. A package of folded disposable absorbent pants, the package comprising:

a housing portion which defines a height dimension, a width dimension, and a depth dimension, the housing portion comprising a front wall and a back wall, each of which extends along the width and height dimensions, the front wall being spaced from the back wall in the depth dimension, wherein the front wall comprises a transparent window region and an opaque border region;

a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion, each pant further defining a waistband region which abuts the waist end and which extends in the transverse direction to at least partially encircle the waist opening, each waistband region comprising a front waistband portion and a back waistband portion, each pant further defining a crotch region which abuts the crotch end;

wherein each of the plurality of pants is folded at least once in the longitudinal direction so as to position the crotch end in close proximity to the waist end, and further wherein each of the plurality of pants is folded twice in the transverse direction such that the first and second side portions of each pant are folded over the respective center portion;

wherein at least a first pant of the plurality of disposable absorbent pants is positioned within the housing portion such that the longitudinal direction of the first pant extends in the height dimension, and such that at least a portion of the waistband region of the first pant is visible through the transparent window region and such that an entirety of the crotch end of the first pant is obscured by the opaque border region, wherein the opaque border region completely surrounds the transparent window region within the front wall.

16. A package of folded disposable absorbent pants, the package comprising:

a housing portion which defines a height dimension, a width dimension, and a depth dimension, the housing portion comprising a front wall and a back wall, each of which extends along the width and height dimensions, the front wall being spaced from the back wall in the depth dimension, wherein the front wall comprises a transparent window region and an opaque border region;

a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion, each pant further defining a waistband region which abuts the waist end and which extends in the transverse direction to at least partially encircle the waist opening, each waistband region comprising a front waistband portion and a back waistband portion, each pant further defining a crotch region which abuts the crotch end;

wherein each of the plurality of pants is folded at least once in the longitudinal direction so as to position the crotch end in close proximity to the waist end, and further wherein each of the plurality of pants is folded twice in the transverse direction such that the first and second side portions of each pant are folded over the respective center portion;

wherein at least a first pant of the plurality of disposable absorbent pants is positioned within the housing portion such that the longitudinal direction of the first pant extends in the height dimension, and such that at least a portion of the waistband region of the first pant is visible through the transparent window region and such that an entirety of the crotch end of the first pant is obscured by the opaque border region;

wherein each pant includes a front panel and a back panel, further wherein for each pant, wherein the front waistband portion comprises a folded-over portion of the front panel, and the back waistband portion comprises a folded-over portion of the back panel, and wherein at least two elastic strands are disposed within the folded-over portion of the front panel and wherein at least two elastic strands are disposed within the folded-over portion of the back panel.

17. A package of folded disposable absorbent pants, the package comprising:
- a housing portion which defines a height dimension, a width dimension, and a depth dimension, the housing portion comprising a front wall and a back wall, each of which extends along the width and height dimensions, the front wall being spaced from the back wall in the depth dimension, wherein the front wall comprises a transparent window region and an opaque border region;
- a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion, each pant further defining a waistband region which abuts the waist end and which extends in the transverse direction to at least partially encircle the waist opening, each waistband region comprising a front waistband portion and a back waistband portion, each pant further defining a crotch region which abuts the crotch end; wherein each pant comprises an absorbent core having a front edge, a back edge spaced from the front edge in the longitudinal direction, and two side edges which extend from the front edge to the back edge;

wherein each of the plurality of pants is folded at least once in the longitudinal direction so as to position the crotch end in close proximity to the waist end, and further wherein each of the plurality of pants is folded twice in the transverse direction such that the first and second side portions of each pant are folded over the respective center portion;

wherein at least a first pant of the plurality of disposable absorbent pants is positioned within the housing portion such that the longitudinal direction of the first pant extends in the height dimension, and such that at least a portion of the waistband region of the first pant is visible through the transparent window region and such that an entirety of the front edge of the absorbent core of the first pant is obscured by the opaque border region.

18. The package of claim 17, wherein the housing portion comprises a carton, wherein the opaque border region comprises paperboard.

19. The package of claim 17, wherein the crotch region of the first pant is at least partially sandwiched between the first side portion of the first pant and the center portion of the first pant.

20. The package of claim 17, wherein the housing portion further comprises a top wall and a bottom wall, each of which extends along the width and depth dimensions, the top wall being spaced from the bottom wall in the height dimension,
wherein the waist end of the first pant is closer to the top wall than to the bottom wall, and wherein the top wall is closer to the crotch end of the first pant than to the waist end of the first pant.

21. The package of claim 17, wherein both the front waistband portion and the back waistband portion of the waistband region of the first pant are wrapped around the crotch region of the first pant.

22. The package of claim 17, wherein the front wall comprises printed text extending in a reading direction, wherein the reading direction extends in the width dimension.

23. The package of claim 17, wherein at least a second pant of the plurality of disposable absorbent pants is positioned within the housing portion such that the longitudinal direction of the second pant extends in the height dimension, and such that at least a portion of the waistband region of the second pant is visible through the transparent window region and such that the front edge of the absorbent core of the second pant is obscured by the opaque border region, the second pant being positioned alongside the first pant in the width dimension.

24. The package of claim 23, wherein the plurality of pants further comprises a first row of pants stacked behind the first pant, the first row extending in the depth dimension between the first pant and the back wall, and wherein the plurality of pants further comprises a second row of pants stacked behind the second pant, the second row extending in the depth dimension between the second pant and the back wall.

25. The package of claim 17, wherein at least the first pant is positioned within the housing portion such that the crotch end of the first pant is obscured by the opaque border region.

* * * * *